United States Patent
Barron et al.

(10) Patent No.: US 9,034,085 B2
(45) Date of Patent: May 19, 2015

(54) ALIPHATIC AMINE BASED NANOCARBONS FOR THE ABSORPTION OF CARBON DIOXIDE

(71) Applicants: Andrew R. Barron, Houston, TX (US); Eoghan Dillon, Houston, TX (US)

(72) Inventors: Andrew R. Barron, Houston, TX (US); Eoghan Dillon, Houston, TX (US)

(73) Assignee: WILLIAM MARSH RICE UNIVERSITY, Houston, TX (US)

( * ) Notice: Subject to any disclaimer, the term of this patent is extended or adjusted under 35 U.S.C. 154(b) by 0 days.

(21) Appl. No.: 14/136,209

(22) Filed: Dec. 20, 2013

(65) Prior Publication Data

US 2014/0103255 A1 Apr. 17, 2014

Related U.S. Application Data

(62) Division of application No. 13/159,289, filed on Jun. 13, 2011, now Pat. No. 8,636,830.

(60) Provisional application No. 61/354,146, filed on Jun. 11, 2010.

(51) Int. Cl.
*B01D 53/02* (2006.01)
*B01J 20/26* (2006.01)
*B01D 53/62* (2006.01)
(Continued)

(52) U.S. Cl.
CPC ............. *B01J 20/261* (2013.01); *B01D 53/025* (2013.01); *B01D 53/62* (2013.01); *B01D 2253/102* (2013.01); *B01D 2253/25* (2013.01); *B01D 2257/504* (2013.01); *B01D 2258/0283* (2013.01); *B82Y 30/00* (2013.01); *B82Y 40/00* (2013.01); *C07D 493/22* (2013.01); *C08K 3/00* (2013.01); *C08K 3/04* (2013.01); *Y02C 10/04* (2013.01); *Y02C 10/08* (2013.01); *Y10S 977/738* (2013.01); *Y10S 977/746* (2013.01);
(Continued)

(58) Field of Classification Search
CPC ..................... B01D 2253/102; B01D 2253/25; B01D 2257/504; B01D 2258/0283; B01D 53/025; B01D 53/62; B01J 20/261; B82Y 30/00; B82Y 40/00; C07D 493/22; C08K 3/00; C08K 3/04; Y02C 10/04; Y02C 10/08
USPC ....... 95/139; 96/154; 525/540; 564/367, 458; 549/513, 543; 977/738, 746, 788, 882, 977/902
See application file for complete search history.

(56) References Cited

U.S. PATENT DOCUMENTS 5,367,051 A * 11/1994 Narang et al. ................ 528/424
6,113,673 A * 9/2000 Loutfy et al. ................... 95/116
(Continued)

OTHER PUBLICATIONS
Synthesis, Characterization and Carbon Dioxide Adsorption of Covalently Attached Polyethyleneimine-Functionalized Single-Wall Carbon Nanotubes by Dillon et al., Published Jan. 2008 by ACSNANO.*

(Continued)

*Primary Examiner* — Christopher P Jones
(74) *Attorney, Agent, or Firm* — Winstead PC

(57) ABSTRACT

A composition of matter, and method to make same, for a nano-based material including a nanocarbon support to which is attached an aliphatic amine. In particular, the composition of matter is an aliphatic amine-nanocarbon material that includes a nanocarbon (NC) support, such as $C_{60}$, nanographite, graphene, nanocarbon ribbons, graphite intercalation compounds, graphite oxide, nano-coal, nanohorns, and combinations thereof, and further includes an aliphatic amine, such as polyethyleneimine (PEI).

11 Claims, 32 Drawing Sheets

(51) Int. Cl.
    *B82Y 30/00*     (2011.01)
    *B82Y 40/00*     (2011.01)
    *C07D 493/22*    (2006.01)
    *C08K 3/00*      (2006.01)
    *C08K 3/04*      (2006.01)

(52) U.S. Cl.
    CPC ........... *Y10S977/788* (2013.01); *Y10S 977/882* (2013.01); *Y10S 977/902* (2013.01)

(56) References Cited

U.S. PATENT DOCUMENTS

| | | | |
|---|---|---|---|
| 7,074,310 B2* | 7/2006 | Smalley et al. | 204/450 |
| 7,511,217 B1* | 3/2009 | Roscheisen et al. | 136/263 |
| 2004/0062989 A1* | 4/2004 | Ueno et al. | 429/217 |
| 2005/0263456 A1* | 12/2005 | Cooper et al. | 210/660 |
| 2006/0046122 A1* | 3/2006 | Chang et al. | 429/33 |
| 2006/0189475 A1* | 8/2006 | Petrik et al. | 502/56 |
| 2007/0099056 A1* | 5/2007 | Kono et al. | 429/34 |
| 2009/0095681 A1* | 4/2009 | Duval et al. | 210/656 |
| 2011/0168018 A1* | 7/2011 | Mohamadalizadeh et al. | 95/136 |
| 2011/0269919 A1* | 11/2011 | Min et al. | 525/540 |
| 2011/0269920 A1* | 11/2011 | Min et al. | 525/540 |

OTHER PUBLICATIONS

Aaron et al., "Separation of CO2 from Flue Gas: A Review", Separation Science and Technology, 2005, 40(1-3): 321-348.

Bates et al., "CO2 capture by a task-specific ionic liquid", J. Am. Chem. Soc., 2002, 124, 926.

Geckler et al., "Polymer-bound C60", J. Am. Chem. Soc., 1993, 115, 3850.

Chattopadhyay et al., "Graphite epoxide", J. Am. Chem. Soc., 2008, 130, 5414.

Strom et al., "Nitrene addition to exfoliated graphene: A one-step route to highly functionalized graphene." Chem. Commun., 2010, 46, 4097.

Knox et al., "Surface modification of porous graphite for ion exchange chromatography", Chromatographia, 1996, 42, 83.

Mallouk et al., "Reversible Intercalation of graphene fluorine: A new bifluoride, C12HF2 and graphene fluorides, $C_xF(5>x>2)$", J. Chem. Soc. Chem. Commun., 102, 1983.

Palchan et al., "Graphite fluoride: An XPS study of a new type of C-F bonding", Chem. Phys. Lett., 1989, 157, 321.

Choi et al., "Adsorbent materials for carbon dioxide capture from large anthropogenic point sources", Chem. Sus. Chem., 2009, 2, 796.

Bourlinos et al., "Graphite oxide: Chemical reduction to graphite and surface modification with primary aliphatic amines and amino acids." Langmuir, 2003, 19, 6050.

Hummers et al., "Preparation of Graphitic oxide", J. Am. Chem. Soc., 1958, 80, 1339.

* cited by examiner

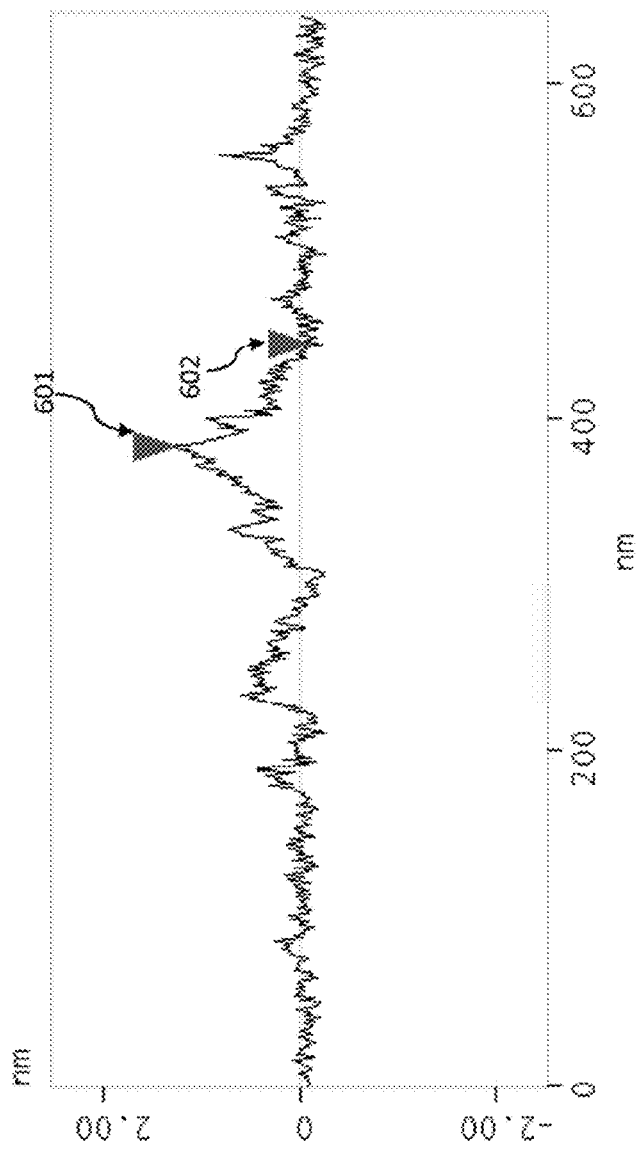

ALIPHATIC AMINE BASED NANOCARBONS FOR THE ABSORPTION OF CARBON DIOXIDE

CROSS-REFERENCE TO RELATED PATENT APPLICATIONS

This application claims priority to: provisional U.S. Patent Application Ser. No. 61/354,146, filed on Jun. 11, 2010, entitled "Polyethyleneimine Based Nanocarbons For the Absorption Of Carbon Dioxide," which provisional patent application is commonly assigned to the assignee of the present invention and is hereby incorporated herein by reference in its entirety for all purposes. This application is a divisional application of U.S. patent application Ser. No. 13/159,289, filed on Jun. 13, 2011, entitled "Aliphatic Amine Based Nanocarbons For the Absorption Of Carbon Dioxide," which patent application is commonly assigned to the assignee of the present invention and is hereby incorporated herein by reference in its entirety for all purposes.

FIELD OF THE INVENTION

The present invention relates to a composition of matter for a nano-based material including a nanocarbon support to which is attached an aliphatic amine. In particular, the present invention relates to aliphatic amine-nanocarbon materials that include a nanocarbon (NC) support, such as $C_{60}$, nanographite, graphene, nanocarbon ribbons, graphite intercalation compounds (GICs), graphite oxide (GO), nano-coal, nanohorns, and combinations thereof, and further include an aliphatic amine, such as polyethyleneimine (PEI). When the aliphatic amine is polyethyleneimine, the composition is a polyethyleneimine-nanocarbon material, also called PEI-NC material.

The present invention also relates to a method for preparing aliphatic amine materials, such as PEI-NC materials.

The present invention also relates to methods removal of carbon dioxide from a source. In particular, the present invention relates to a method for removal of carbon dioxide from a gas source formed from the combustion of a hydrocarbon or carbon material such as coal.

BACKGROUND OF THE INVENTION

Carbon capture and storage (CCS) is a means of mitigating the contribution of fossil fuel emissions to global warming, based on capturing carbon dioxide ($CO_2$) from large point sources such as fossil fuel power plants, and storing it away from the atmosphere by different means.

Carbon sequestration is a geoengineering technique for long-term storage of carbon dioxide or other forms of carbon to mitigate global warming. Carbon dioxide is usually captured from the atmosphere through biological, chemical or physical processes. It has been proposed as a way to mitigate accumulation of greenhouse gases in the atmosphere, which are released by burning fossil fuels. Carbon dioxide may be captured as a pure by-product in processes related to petroleum refining or from flue gases from power generation. Carbon dioxide sequestration can then be synonymous with the storage part of carbon capture and storage, which refers to large-scale, permanent artificial capture and sequestration of industrially-produced carbon dioxide using subsurface saline aquifers, reservoirs, ocean water, aging oil fields, or other carbon sinks.

Various scrubbing processes have been proposed to remove carbon dioxide from the air, or from flue gases. These usually involve using a variant of the Kraft process. Scrubbing processes may be based on sodium hydroxide. The carbon dioxide is absorbed into solution, transferred to lime and released in a kiln. With some modifications to the existing processes, mainly an oxygen-fired kiln, the end result is a concentrated stream of carbon dioxide ready for storage or use in fuels. An alternative to this thermo-chemical process is an electrical one in which an electrical voltage is applied across the carbonate solution to release the carbon dioxide. While simpler, the electrical process consumes more energy as it splits water at the same time. It also depends on electricity and so unless the electricity is renewable, the carbon dioxide produced during electricity production has to be taken into account. The early incarnations of air capture used electricity as the energy source and therefore depended on carbon-free sources. A thermal air capture system uses heat that can be generated on-site, reducing the inefficiencies associated with producing electricity, but of course it still needs a source of (carbon-free) heat. Concentrated solar power is an example of such a source.

Some examples of carbon dioxide capture onto a salt are the following. First, carbon dioxide is absorbed by an alkaline NaOH solution to produce dissolved sodium carbonate. The carbonate ion is removed from the solution by reaction with calcium hydroxide ($Ca(OH)_2$), which results in the precipitation of calcite ($CaCO_3$). The causticization reaction is a mildly exothermic, aqueous reaction that occurs in an emulsion of calcium hydroxide.

As an alternative to sequestration, the recycling carbon dioxide is likely to offer the most environmentally and financially sustainable response to the global challenge of significantly reducing greenhouse gas emissions from major stationary (industrial) emitters in the near to medium term. This is because newly developed technologies, such as Bio CCS Algal Synthesis value captured, pre-smokestack carbon dioxide (such as from a coal fired power station, for example) as a useful feedstock input to the production of oil-rich algae in solar membranes to produce oil for plastics and transport fuel (including aviation fuel) and nutritious stockfeed for farm animal production.

Zeolite based $CO_2$ scrubbers suffer from many of the same disadvantages that have been previously mentioned for the broader category of adsorption based scrubbers. Mainly a substantial decrease in $CO_2$ uptake is achieved even with only minor increases in operating temperature. Furthermore the presence of even a small amount of moisture in the system can also greatly reduce the $CO_2$ uptake capacity for zeolite material. For example, CaX, which is one of the best performing zeolites, can have its $CO_2$ uptake capacity reduced from 2.5 mmol $CO_2$ per gram of absorbent to 0.1 mmol $CO_2$ per gram of absorbent with a $H_2O$ concentration change from 1 wt % to 16 wt %. This in combination with decrease in capacity with temperature means that the zeolite scrubbers may only be operated at very mild conditions, which are not found in industrial flue gas streams.

The adsorption capacities of activated carbons behave in a similar way to those of zeolites, with rapidly decreasing capacities with slight temperature increases. An example of this is the decrease in $CO_2$ capacity from 3.2 mmol $CO_2$ per gram of adsorbent to 1.5 mmol $CO_2$ per gram of adsorbent with only a slight increase in temperature, from 288 K to 328 K, using Ajax activate carbon as the test scrubber. Also similar to Zeolites the adsorption capacity is greatly affected by the presence of water in the system. An example of this is the decrease in $CO_2$ uptake from 4 mmol $CO_2$ per gram of adsorbent to 1 mmol $CO_2$ per gram of adsorbent when dry coconut shell carbon was wet. These moisture effects only effect the $CO_2$ uptake capacities at low pressures (<25 bar), however the operating costs to pressurize the activate carbon to above 25 bar will come with a large energy penalty.

Calcium oxide based scrubbers do have a very large capacity for $CO_2$ uptake with one very large drawback. In order for the scrubber to achieve a large loading (~13.4 mmol $CO_2$ per gram of adsorbent) they have to be operated at very high temperatures, ~1000 K. Also, the practical use of these as large scale $CO_2$ scrubbers is limited by the rate of chemical reaction. This rate is usually very high at massively elevated temperatures (~1000 K). This additional heating will also incur a very large energy penalty on the system. Furthermore, calcium oxide based scrubber systems suffer from rapid degradation of $CO_2$ uptake capacity during repeated cycling of the system, this is mainly due to pore blocking and adsorbent sintering.

Amine gas treating, also known as gas sweetening and acid gas removal, refers to a group of processes that use aqueous solutions of various alkanolamines (commonly referred to simply as amines) to remove hydrogen sulfide ($H_2S$) and carbon dioxide ($CO_2$) from gases. It is a common unit process used in refineries, petrochemical plants, natural gas processing plants and other industries. Amines are organic compounds and functional groups that contain a basic nitrogen atom with a lone pair. A typical amine gas treating process includes an absorber unit and regenerator unit as well as accessory equipment. In the absorber, the downflowing amine solution absorbs $H_2S$ and $CO_2$ from the upflowing sour gas to produce a sweetened gas stream (i.e., an $H_2S$-free gas) as a product and an amine solution rich in the absorbed acid gases. The resultant "rich" amine is then routed into the regenerator (a stripper with a reboiler) to produce regenerated or "lean" amine that is recycled for reuse in the absorber.

Monoethanolamine (MEA) is the current industrial standard for carbon dioxide capture from industrial flue gas streams despite several disadvantages to the system. The temperature manipulation required for the regeneration of the scrubber system is responsible for up to 70-80% of the operating cost of the scrubber system. Furthermore, as it is a solvent based system, the solvent containing the MEA has to be constantly pumped from one tower to another for absorption and regeneration. The solvent used also has to be constantly replaced due to solvent loss, as the system has to be heated to high temperatures ~120° C. to regenerate the scrubber. The solvent is also degraded by several other factors including; the high temperature of the flue gas stream itself which is over 100° C. above the ideal temperature for MEA. (See D. Aaron and C. Tsouris, Separation of $CO_2$ from Flue Gas: A Review, Separation Science and Technology, 40:1).

Several approaches have been made to improve the amine process. For example, designing ionic liquids with greater selectivity (E. D. Bates, R. D. Mayton, I. Ntai, and J. H. Davis, Jr., "$CO_2$ capture by a task-specific ionic liquid", *J. Am. Chem. Soc.*, 2002, 124, 926).

The separation of carbon dioxide from industrial scale coal fired power plants has garnered a lot of attention as the debate regarding climate change intensifies.

SUMMARY OF THE INVENTION

In general, in one aspect, the invention features a method that includes selecting a nanocarbon support. The nanocarbon support is $C_{60}$, nano-graphite, graphene, nanocarbon ribbons, graphite intercalation compounds, graphite oxide, nano-coal, nanohorns, or a combination thereof. The method further includes attaching an aliphatic amine to the nanocarbon support to form an aliphatic amine-nanocarbon material.

Implementations of the inventions can include one or more of the following features:

The aliphatic amine-nanocarbon material can be capable of absorbing $CO_2$ at ambient pressure and temperature in an amount that is at least about 10 wt % of the aliphatic amine-nanocarbon material.

The nanocarbon support can be $C_{60}$, and the aliphatic amine-nanocarbon material can be an aliphatic amine-$C_{60}$ material.

The aliphatic amine can be polyethyleneimine, and the aliphatic amine-nanocarbon material can be a polyethyleneimine-nanocarbon material.

The polyethyleneimine-nanocarbon material can be capable of absorbing $CO_2$ at ambient pressure and temperature in an amount that is at least about 10 wt % of the polyethyleneimine-nanocarbon material.

The polyethyleneimine-nanocarbon material can be capable of absorbing $CO_2$ at ambient pressure and temperature in an amount that is at least about 15 wt % of the polyethyleneimine-nanocarbon material.

The polyethyleneimine-nanocarbon material can be capable of absorbing $CO_2$ at ambient pressure and temperature in an amount that is at least about 20 wt % of the polyethyleneimine-nanocarbon material.

The polyethyleneimine-nanocarbon material can be capable of absorbing $CO_2$ at ambient pressure and temperature in an amount that is between about 20 wt % and about 25 wt % of the polyethyleneimine-nanocarbon material.

The nanocarbon support can be $C_{60}$, and the polyethyleneimine-nanocarbon material can be a polyethyleneimine-C60 material.

The nanocarbon support can include graphite oxide, and the polyethyleneimine-nanocarbon material can include a polyethyleneimine-graphite oxide material.

The step of attaching can include reacting an epoxy group of the graphite oxide with the polyethyleneimine.

The method can further include dispersing the polyethyleneimine in ethanol via bath sonication to form a polyethyleneimine solution. The method can further include adding triethylamine to the polyethyleneimine solution to keep the primary amines of the polyethyleneimine unprotonated. The method can further include dispersing the graphite oxide in water to form a graphite oxide solution. The method can further include mixing the polyethyleneimine solution and the graphite oxide solution to form the polyethyleneimine-graphite oxide material.

The nanocarbon support can include a graphite intercalation compound, and the polyethyleneimine-nanocarbon material can include a polyethyleneimine-graphite intercalation compound material.

The polyethyleneimine can be unfolded during the step of attaching the polyethyleneimine to the nanocarbon support.

The polyethyleneimine can be unfolded to expose its tertiary amines such that over there the ratio of (a) tertiary amines operable for absorbing $CO_2$ at ambient pressure and temperature to (b) primary amines and secondary amines operable for absorbing $CO_2$ at ambient pressure and temperature is at least about 5:1.

The ratio can be at least about 10:1.

The method can further include removing impurities from being in the aliphatic amine-nanocarbon material.

The impurities can be nitrogen oxide, sulfur dioxide, or a combination thereof.

In general, in another aspect, the invention features a method that includes selecting an aliphatic amine-nanocarbon material. The nanocarbon support is $C_{60}$, nano-graphite, graphene, nanocarbon ribbons, graphite intercalation compounds, graphite oxide, nano-coal, nanohorns, or a combination thereof. The method further includes using the aliphatic amine-nanocarbon material to absorb carbon dioxide.

Implementations of the above inventions can include one or more of the following features:

The aliphatic amine-nanocarbon material can absorb $CO_2$ in an amount that is at least about 10 wt % of the aliphatic amine-nanocarbon material.

The nanocarbon support can be $C_{60}$, and the aliphatic amine-nanocarbon material can be an aliphatic amine-$C_{60}$ material.

The aliphatic amine can be polyethyleneimine, and the aliphatic amine-nanocarbon material can be a polyethyleneimine-nanocarbon material.

The polyethyleneimine-nanocarbon material can absorb $CO_2$ in an amount that is at least about 10 wt % of the polyethyleneimine-nanocarbon material.

The polyethyleneimine-nanocarbon material can absorb $CO_2$ in an amount that is at least about 15 wt % of the polyethyleneimine-nanocarbon material.

The polyethyleneimine-nanocarbon material can absorb $CO_2$ in an amount that is at least about 20 wt % of the polyethyleneimine-nanocarbon material.

The polyethyleneimine-nanocarbon material can absorb $CO_2$ in an amount that is between about 20 wt % and about 25 wt % of the polyethyleneimine-nanocarbon material.

The nanocarbon support can be $C_{60}$, and the polyethyleneimine-nanocarbon material can be a polyethyleneimine-$C_{60}$ material.

The nanocarbon support can include graphite oxide, and the polyethyleneimine-nanocarbon material can include a polyethyleneimine-graphite oxide material.

The nanocarbon support can include a graphite intercalation compound, and the polyethyleneimine-nanocarbon material can include a polyethyleneimine-graphite intercalation compound material.

The ratio of (a) tertiary amines of the polyethyleneimine-nanocarbon material operable for absorbing $CO_2$ to (b) primary amines and secondary amines of the polyethyleneimine-nanocarbon material operable for absorbing $CO_2$ can be at least about 5:1.

The ratio can be at least about 10:1.

The polyethyleneimine-nanocarbon material can be used as a carbon dioxide scrubber.

The carbon dioxide scrubber can be a regenerable carbon dioxide scrubber.

The polyethyleneimine-nanocarbon material can be used as a carbon dioxide scrubber is used in a small confined area.

The small confined area is a space shuttle, submarine, or a scuba suit.

The polyethyleneimine-nanocarbon material can be used as a carbon dioxide scrubber in the separation of carbon dioxide from flue gas streams.

The flue gas system can be in an industrial scale coal fired power plant.

In general, in another aspect, the invention features a

A composition that includes a nanocarbon support. The nanocarbon support is $C_{60}$, nano-graphite, graphene, nano-carbon ribbons, graphite intercalation compounds, graphite oxide, nano-coal, nanohorns, or a combination thereof. The composition further includes an aliphatic amine attached to the nanocarbon support to form an aliphatic amine-nanocarbon material.

Implementations of the above inventions can include one or more of the following features:

The aliphatic amine-nanocarbon material can have a $CO_2$ absorption capacity at ambient pressure and temperature of at least about 10 wt % of the aliphatic amine-nanocarbon material.

The nanocarbon support can be $C_{60}$, and the aliphatic amine-nanocarbon material can be an aliphatic amine-$C_{60}$ material.

The aliphatic amine can be polyethyleneimine, and the aliphatic amine-nanocarbon material can be a polyethyleneimine-nanocarbon material.

The polyethyleneimine-nanocarbon material can have a $CO_2$ absorption capacity at ambient pressure and temperature of at least about 10 wt % of the polyethyleneimine-nanocarbon material.

The polyethyleneimine-nanocarbon material can have a $CO_2$ absorption capacity at ambient pressure and temperature of at least about 15 wt % of the polyethyleneimine-nanocarbon material.

The polyethyleneimine-nanocarbon material can have a $CO_2$ absorption capacity at ambient pressure and temperature of at least about 20 wt % of the polyethyleneimine-nanocarbon material.

The polyethyleneimine-nanocarbon material can have a $CO_2$ absorption capacity at ambient pressure and temperature between about 20 wt % and about 25 wt % of the polyethyleneimine-nanocarbon material.

The nanocarbon support can be $C_{60}$, and the polyethyleneimine-nanocarbon material can be a polyethyleneimine-$C_{60}$ material.

The nanocarbon support can include graphite oxide, and the polyethyleneimine-nanocarbon material can include a polyethyleneimine-graphite oxide material.

The nanocarbon support can include a graphite intercalation compound, and the polyethyleneimine-nanocarbon material can include a polyethyleneimine-graphite intercalation compound material.

The polyethyleneimine in the polyethyleneimine-nanocarbon material can be unfolded.

The ratio of (a) tertiary amines of the polyethyleneimine-nanocarbon material operable for absorbing $CO_2$ at ambient pressure and temperature to (b) primary amines and secondary amines of the polyethyleneimine-nanocarbon material operable for absorbing $CO_2$ at ambient pressure and temperature can be at least about 5:1.

The ratio can be at least about 10:1.

In general, in another aspect, the invention features a composition that includes a nanocarbon support and an aliphatic amine attached to the nanocarbon support to form an aliphatic amine-nanocarbon material. The aliphatic amine-nanocarbon material has a $CO_2$ absorption capacity at ambient pressure and temperature of at least about 15 wt % of the aliphatic amine-nanocarbon material.

DESCRIPTION OF DRAWINGS

For a more detailed understanding of the preferred embodiments, reference is made to the accompanying figures, wherein:

FIGS. 6A-6C is a sectional analysis of the PEI-$C_{60}$ shown in FIG. 5A.

FIG. 6A is the AFM image of FIG. 5A that shows where the sectional analysis was performed. FIG. 6B is a graph showing the spectrum of the sectional analysis. FIG. 6C is a graph showing the results of the sectional analysis.

DETAILED DESCRIPTION

The present invention relates to aliphatic amine-nanocarbon materials that include a nanocarbon (NC) support, such as $C_{60}$, nano-graphite, graphene, nanocarbon ribbons, graphite intercalation compounds, graphite oxide, nano-coal, nano-horns, and combinations thereof, or a similar carbon rich nanomaterial, and further include an aliphatic amine, such as polyethyleneimine (PEI). The fabrication of a polyethyleneimine (PEI) based $CO_2$ scrubber has been achieved. Nanocarbon (NC) materials can be used as substrate for the PEI. As compared with single-wall carbon nanotubes, much less expensive nanocarbon supports (such $C_{60}$, nano-graphite, graphene, nanocarbon ribbons, graphite intercalation compounds, graphite oxide, nano-coal, nanohorns, and combinations thereof) can be used, which can provide similar or significantly improved materials. Embodiments of the present invention are capable of absorbing at least about 10% of its weight in $CO_2$ at ambient pressure and temperature. Some embodiments of the present invention are capable of absorbing at least about 15% of its weight in $CO_2$ at ambient pressure and temperature. Some embodiments of the present invention are capable of absorbing at least about 20% of its weight in $CO_2$ at ambient pressure and temperature. Some embodiments of the present invention are capable of absorbing between about 20% and about 25% of its weight in $CO_2$ at ambient pressure and temperature.

Using nanocarbons gives the absorption system a large surface area, which is critical in any absorption system. Furthermore, the scrubber material is a solid rather that a liquid based system. This significantly cuts the regeneration costs for several reasons, such as the requirement of additional solvent after regeneration, which is the case in the current industrial standard, monoethanol amine (MEA). Additionally, regeneration temperature is significantly lower than a liquid based system, ~75° C. for the PEI-NC system compared to ~120° C. for MEA.

Figure 1:
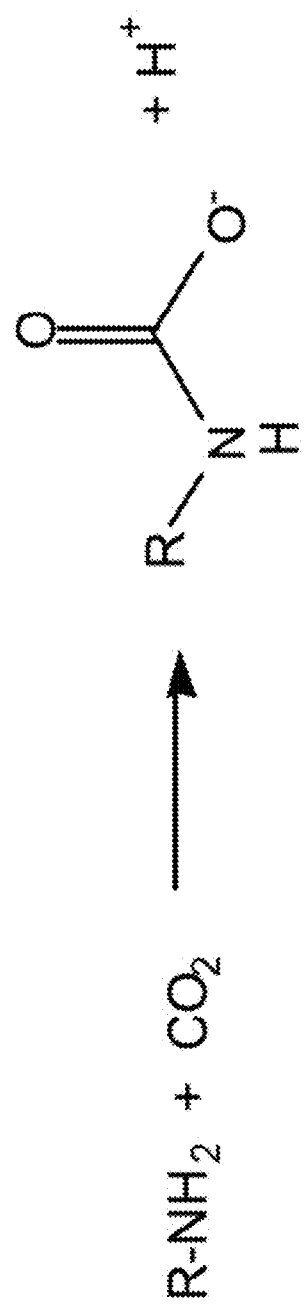
FIG. 1 is a schematic diagram of $CO_2$ absorption onto an amine-based scrubber.

Polyethyleneimine and MEA capture $CO_2$ by means of a carbamate reaction, the reaction scheme for which is shown in FIG. 1.

PEI-functionalization was advantageous based upon studies of the Applicants that showed the polyethyleneimine once covalently bound to a SWNT was not only immobilized, but was able to absorb a larger weight percentage of a reactive species than the free polymer was not. (E. P. Dillon, C. A. Crouse, A. R. Barron, Synthesis, characterization, and carbon dioxide adsorption of covalently attached polyethyleneimine-functionalized single-wall carbon nanotubes. *ACS Nano*, 2008, 2, 156).

The separation of carbon dioxide from industrial scale coal fired power plants has garnered a lot of attention as the debate regarding climate change intensifies. By using embodiments of the present invention, carbon dioxide will be captured from any flue gas stream or confined area containing $CO_2$. Embodiments of the present invention work via the reaction of $CO_2$ and amine functionalities via a carbamate reaction, as shown in FIG. A. Furthermore, the amine functionalities are grafted to a nanocarbon backbone, which gives a large surface area for absorption.

Figure 2:
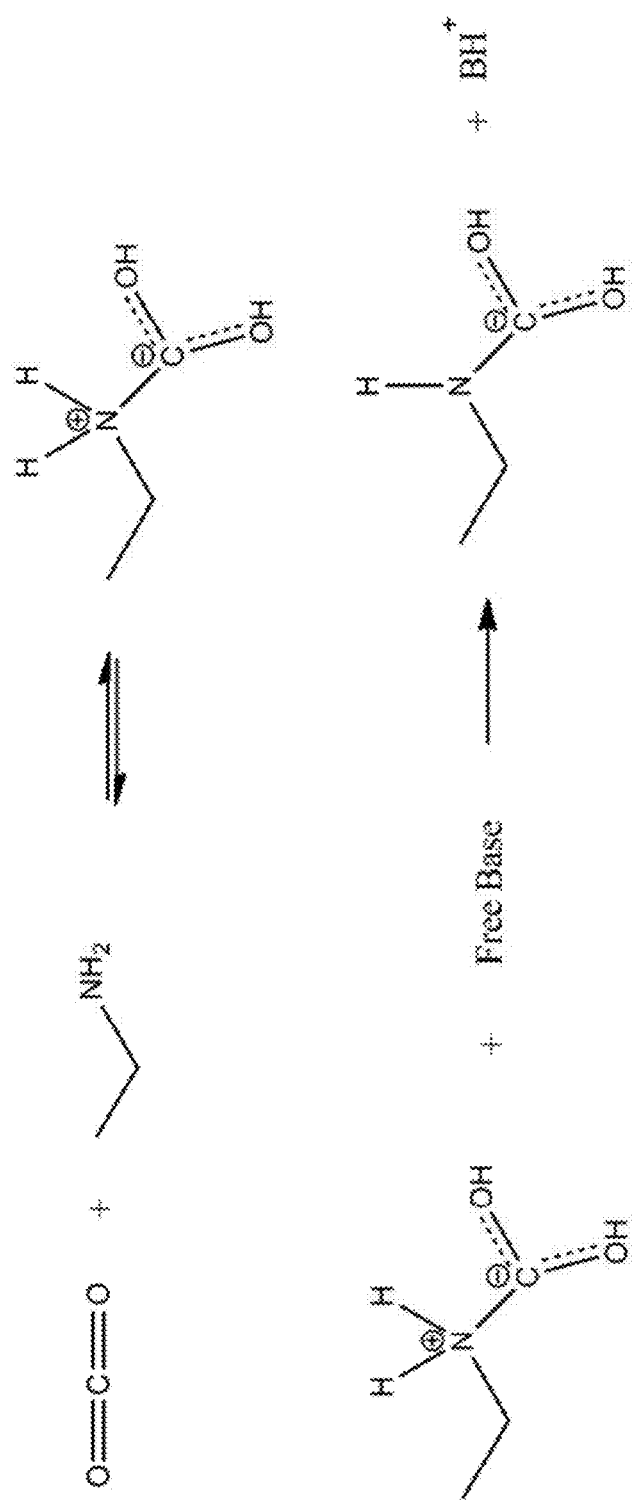
FIG. 2 shows the reaction mechanism between primary and secondary amines and $CO_2$.

Polyethyleneimine can be a linear or branched polymer of molecular weights varying from <600 Da. to >800,000 Da. In the linear form PEI is terminated with a primary amine group at each end and a chain consisting of secondary amines with ethylene groups on either side. The branched polymer can have varying degrees of primary, secondary and tertiary amines depending on synthesis techniques. Generally it is assumed that the ratio between them is 1:1:1. Primary and secondary amines react in the same way with $CO_2$, however, the reaction between tertiary amines and $CO_2$ is slightly different. FIG. 2 shows the reaction mechanism between primary and secondary amines and $CO_2$.

In an aqueous scrubber system the free base is usually $H_2O$ or $OH^-$ or another amine. When the PEI-NC system is compared to any adsorption system it is noticed that the addition of $H_2O$ to the system will have the opposite effect. In the adsorption system the additional $H_2O$ will compete with the $CO_2$ to be adsorbed, greatly reducing the adsorption capacity of the scrubber. However, in the PEI-NC system the addition of water, which is present in flue gas streams, actually enhances the adsorption capacity of the system providing additional free base to the system. It is also noted that in dry conditions the efficiency of an amine based scrubber is 0.5 mol $CO_2$ per mol N, whereas, in wet conditions $H_2O$ can act as a free base and the efficiency of the amines to absorb $CO_2$ is doubled to 1 mol $CO_2$ per mol N.

Figure 3:
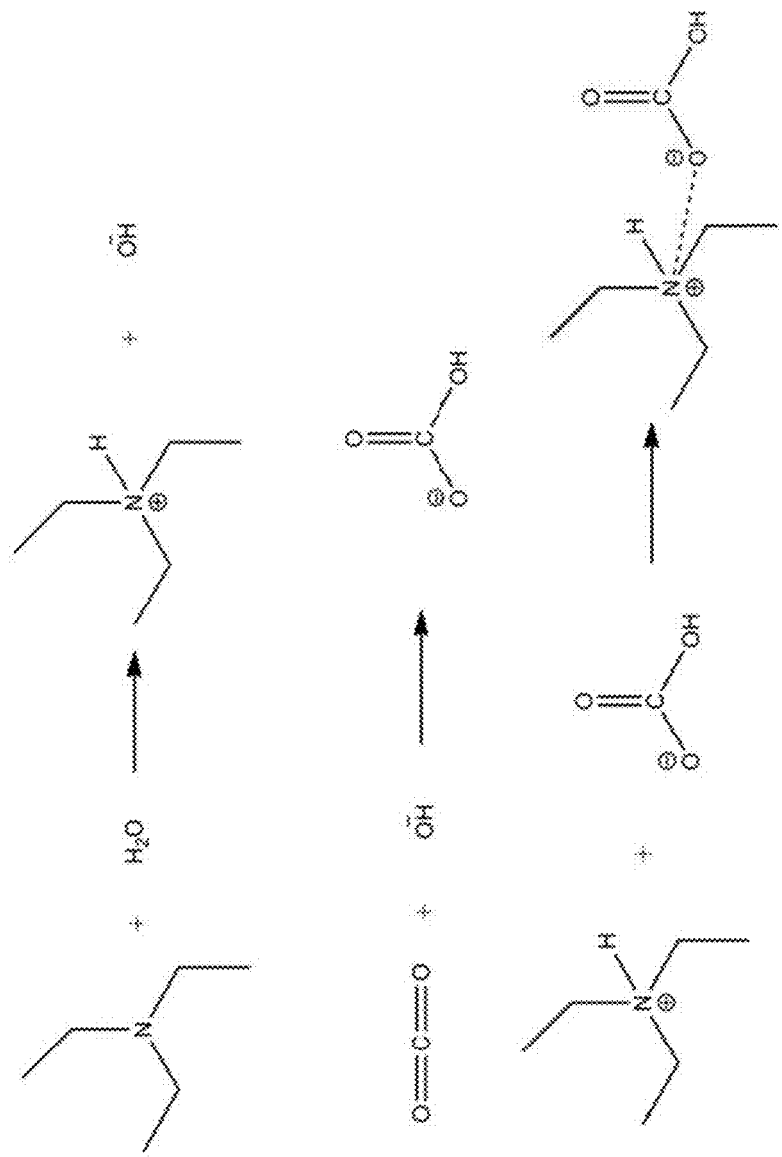
FIG. 3 shows the reaction scheme for $H_2O$ used in the absorption mechanism of tertiary amines.

$H_2O$ is also used in the absorption mechanism of tertiary amines. The reaction scheme for this is shown in FIG. 3.

This illustrates an advantage of the PEI-NC system over adsorption based system in that it allows for absorption to occur for primary, secondary, and tertiary amines. It has been found in some embodiments of the present invention that the unfolding of the PEI exposes the tertiary amines which increases the ability for the absorption mechanism of tertiary amines to occur, which substantially increases the absorption capacity of the material.

Also, by tethering the PEI to a solid backbone, this will further enhance the overall performance and efficiency of the scrubber system. One of the large energy costs associated with an aqueous based scrubber, such as monoathanolamine, is the cost of heating the solvent. By tethering the PEI to a solid substrate—graphite in this case—the heat capacity of the system has been reduced to 0.71 kJ kg$^{-1}$ K$^{-1}$ from 4.2 kJ kg$^{-1}$ K$^{-1}$ for $H_2O$ in embodiments of the present invention thus reducing the energy penalty of the overall system.

Additionally the regeneration of a MEA system requires temperatures of ~120° C. while regeneration of the PEI-NC system has been shown by our experiments to be ~75° C. Also, the heating of MEA repeatedly to ~120° C. can cause degradation to the scrubber and thus corrosion of the reaction vessel. Considering these factors shows the ability of the PEI-NC scrubber to overcome the disadvantages associated with solvent based scrubbers while still further decreasing the energy penalty associated with a $CO_2$ capture system.

When compared to membrane diffusion, cryogenic distillation and gas hydrate formation the PEI-NC system also has none of the disadvantages associated with these systems. Membrane diffusion has been shown to be either unselective or impermeable to $CO_2$. As the PEI-NC system is a chemisorption process, it will be much more selective to $CO_2$ over $H_2O$. The cryogenic distillation process requires a high purity stream of $CO_2$ which the PEI-NC system does not. While $H_2O$ can cause pipe plugs in the cryogenic distillation it actively enhances the absorption efficiency in the PEI-NC system. The case is the same for the gas hydrate process, low temperatures can cause the line to plug, while the PEI-NC system can operate even more efficiently at lower temperatures without these issues.

Taking all these factors into account, the superior performance of PEI-NC is evident. None of the disadvantages associated with any of the other system impede the absorption efficiency of the PEI-NC system. In fact some of the disadvantages to the other systems are assets to the PEI-NC, such as the effect of water on absorption. (See S. Choi, J. H. Drese, C. W. Jones, Adsorbent materials for carbon dioxide capture from large anthropogenic point sources, *Chem. Sus. Chem.*, 2009, 2, 796).

According to one aspect of the present invention there is provided for a composition of matter comprise polyethyleneimine, of any molecular weight and degree of branching, and a nanocarbon substrate such as $C_{60}$, nano-graphite, graphene, nanocarbon ribbons, graphite intercalation compounds, graphite oxide, nano-coal, nanohorns, and combinations thereof.

The PEI-NC can be used as a new regenerable carbon dioxide scrubber for use in small confined areas such as a space shuttle, submarine, or scuba suits and for use in the separation of carbon dioxide from large scale flue gas streams.

PEI-CN Materials

The method of attachment of the PEI to the NC can be achieved in several ways. The following examples that are provided are not intended to limit the scope of the invention but to illustrate several methods that can be utilized in embodiments of the invention.

Example 1

PEI-$C_{60}$ Material $C_{60}$ (100 mg) were dispersed in toluene (50 ml) via bath sonication. Concurrently branched 25,000 Da. polyethyleneimine (1 g) was solubilized in chloroform (50 ml). The two solutions were combined rapidly with vigorous stirring. The reaction was allowed to proceed until all the product had crashed out of solution, approximately 1 week. The product was then recovered via filtration through a 200 nm pore size PTFE filter. The product was removed from the vessel sidewalls by bath sonication in chloroform, filtered and washed with copious amounts of chloroform to remove any unreacted polyethyleneimine.

Carbon dioxide uptake analysis was performed using a Seiko TGA. The PEI-$C_{60}$ was placed in a platinum pan and placed in the balanced TGA. The oven was sealed and the temperature raised to 125° C. to burn off any residual $CO_2$ and solvent.

Figure 4A:
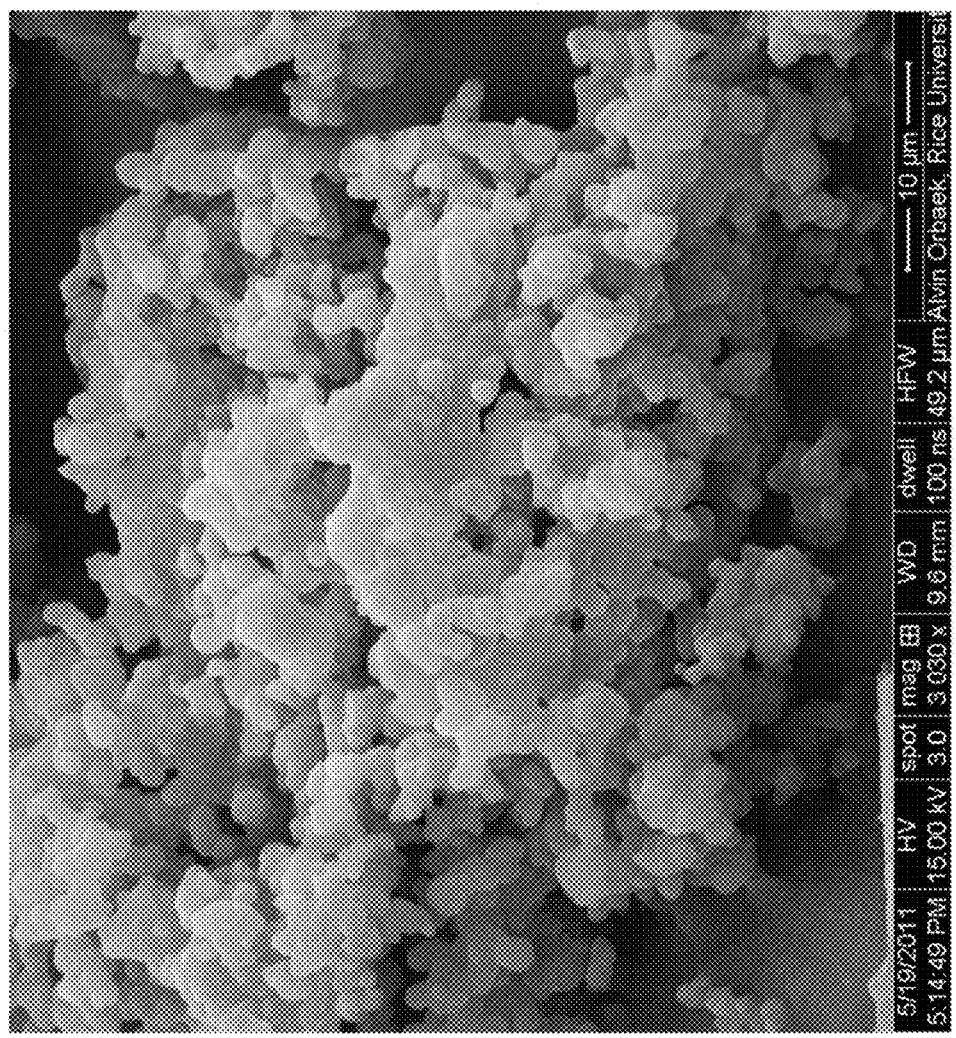
FIGS. 4A-4C are SEM images of PEI-$C_{60}$.
Figure 4B:
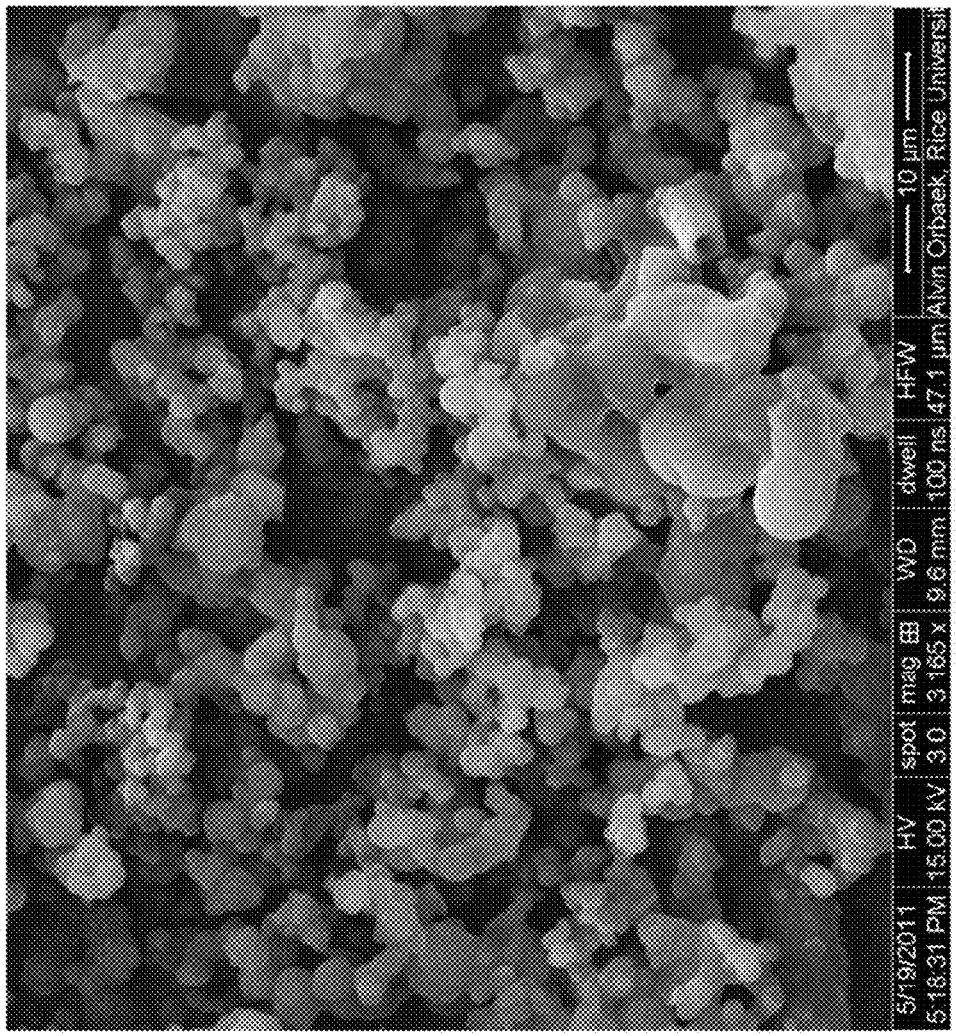
Figure 4C:
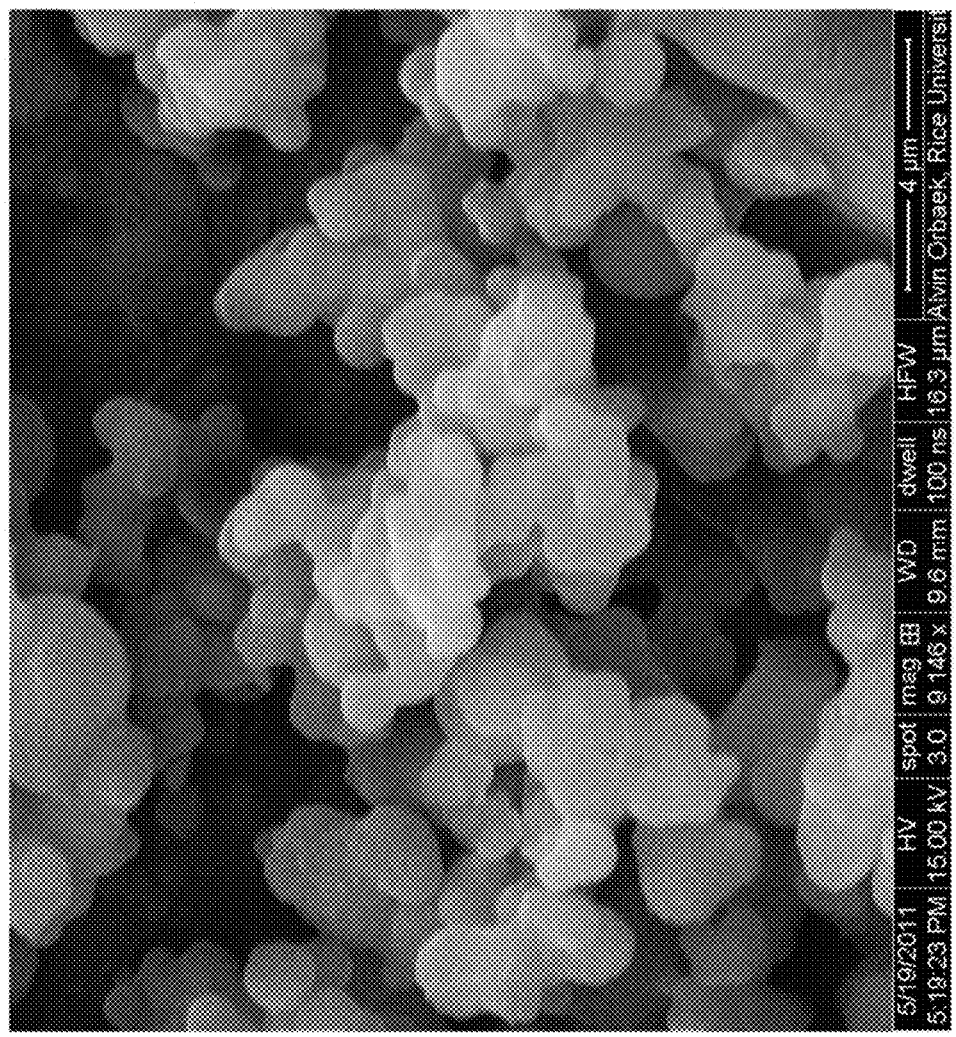
Figure 5A:
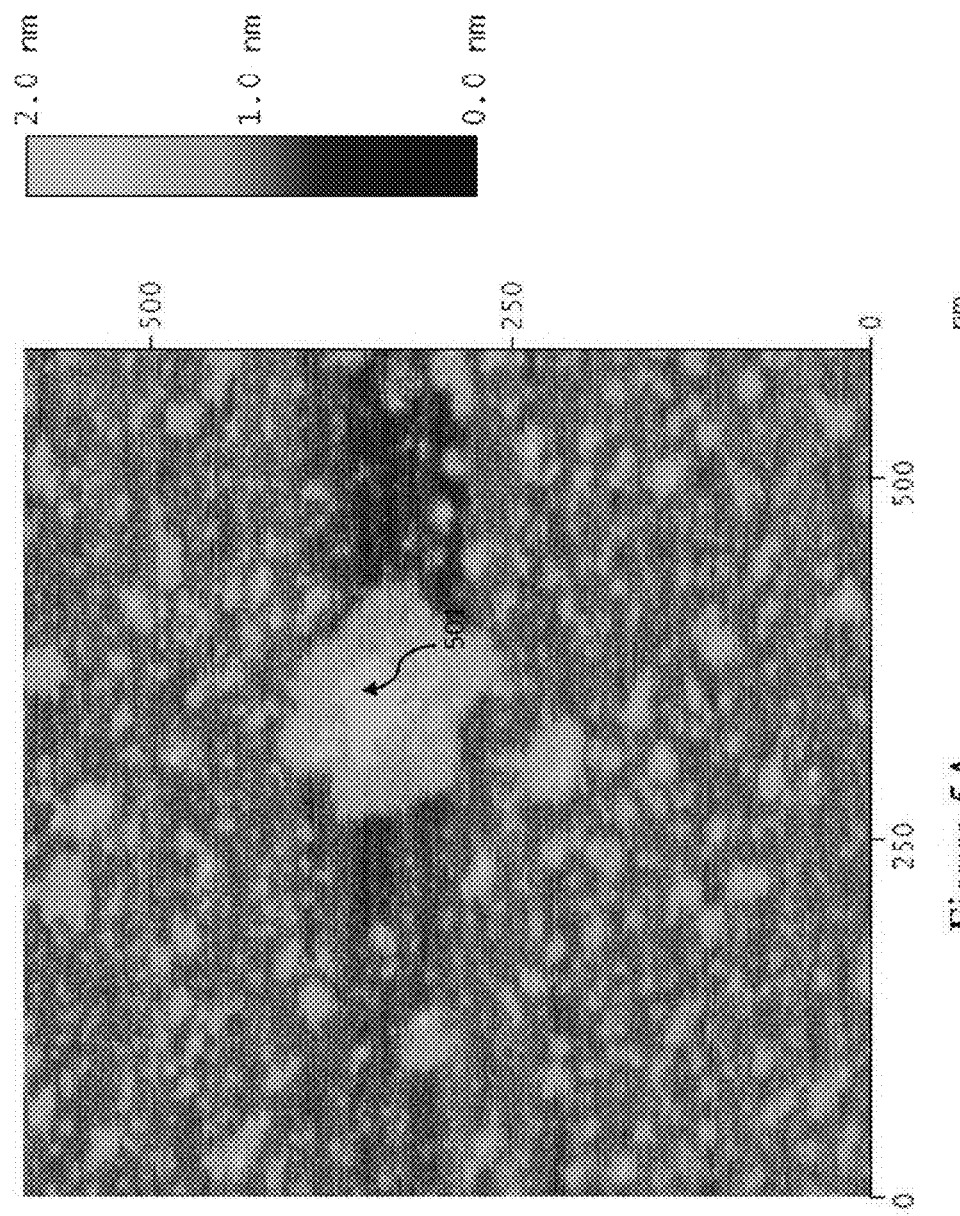
FIGS. 5A-5C are AFM images of PEI-$C_{60}$.
Figure 5B:
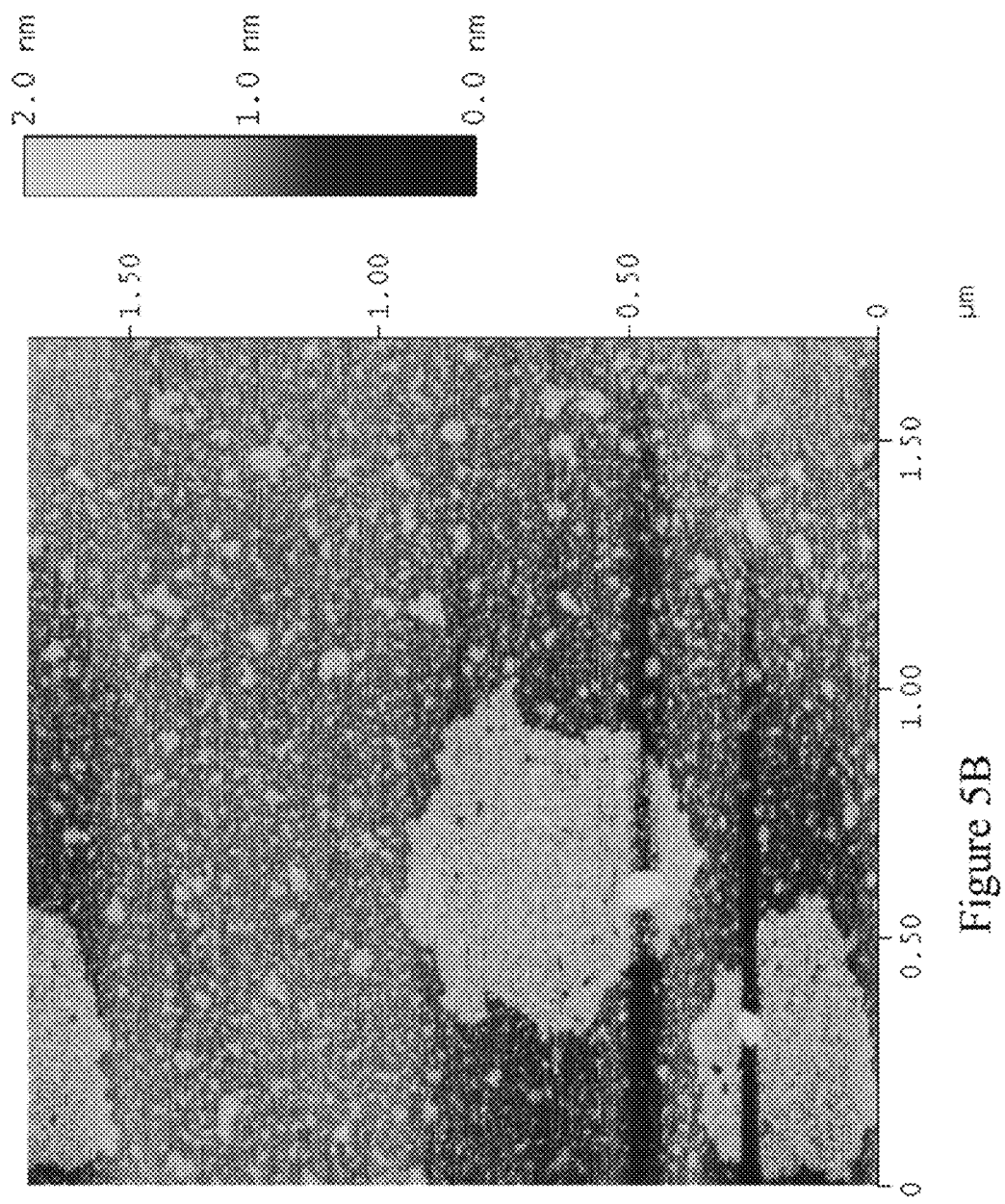
Figure 5C:
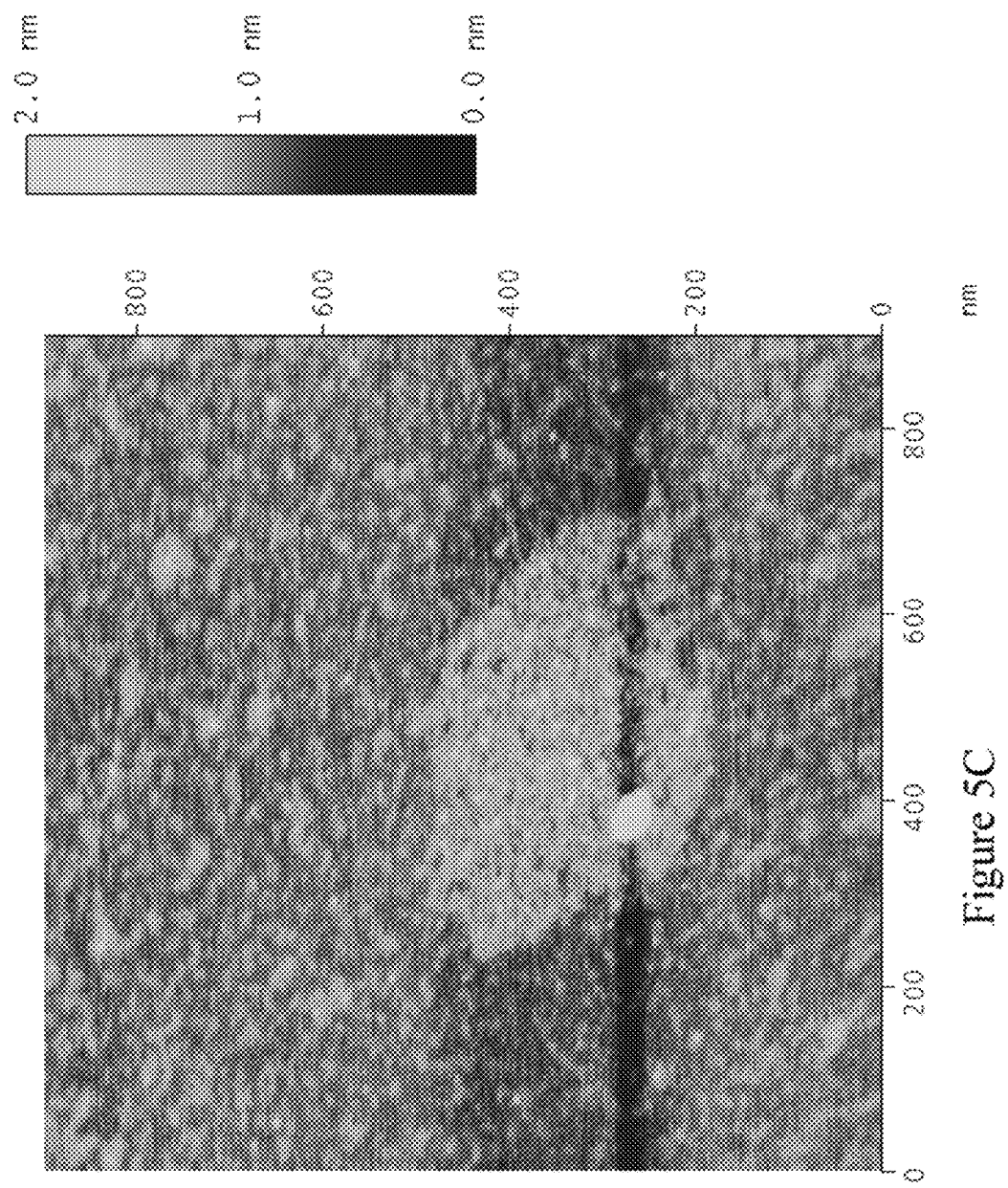

FIGS. 4A-4C are SEM images of the PEI-$C_{60}$ produced by this method. FIGS. 5A-5C are AFM images of the PEI-$C_{60}$ produced by this method using a Digital Instruments NanoScope. For each of the AFM images of FIGS. 5A-5C, (a) the scan rate was 1.001 Hz, (b) the number of samples was 512, (c) the image data was height, and (d) the data scale was 2.000 nm. The scan size for the AFM images of FIGS. 5A-5C was 589.8 nm, 1706 nm, and 900.6 nm, respectively.

Figure 6A:
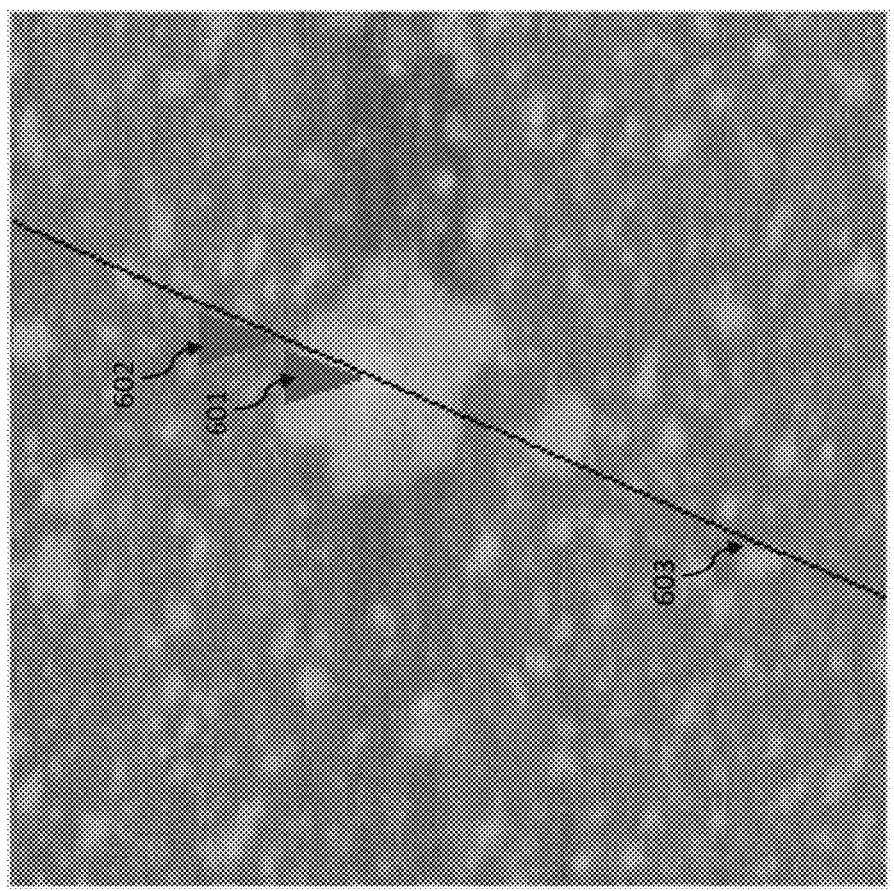
Figure 6B:
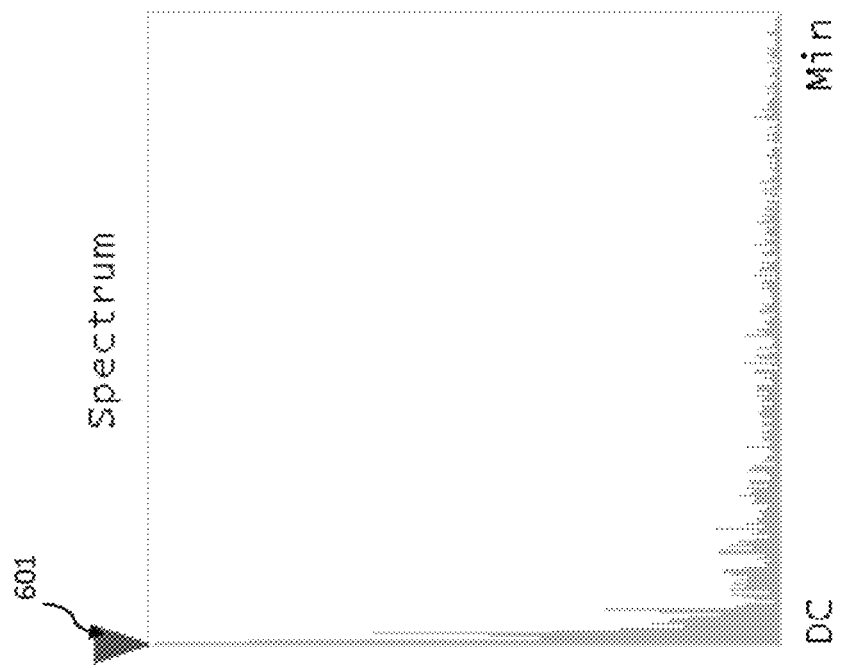

The AFM images of FIGS. 5A-5C show that the PEI had unfolded. The heightened areas shown in FIGS. 5A-5C (such as at 501) was $C_{60}$ to which the PEI had bound. FIGS. 6A-6C is a sectional analysis of the embodiment of the PEI-$C_{60}$ shown in FIG. 5A. FIG. 6A is the AFM image of FIG. 5A that shows where the sectional analysis was performed (along line 603 with portions 601 and 602 along that line). FIG. 6B is a graph showing the spectrum of the sectional analysis. FIG. 6C is a graph showing the results of the sectional analysis. This sectional analysis confirmed that the PEI had unfolded and the heightened areas were the $C_{60}$ (the nanocarbon support).

Figure 7:
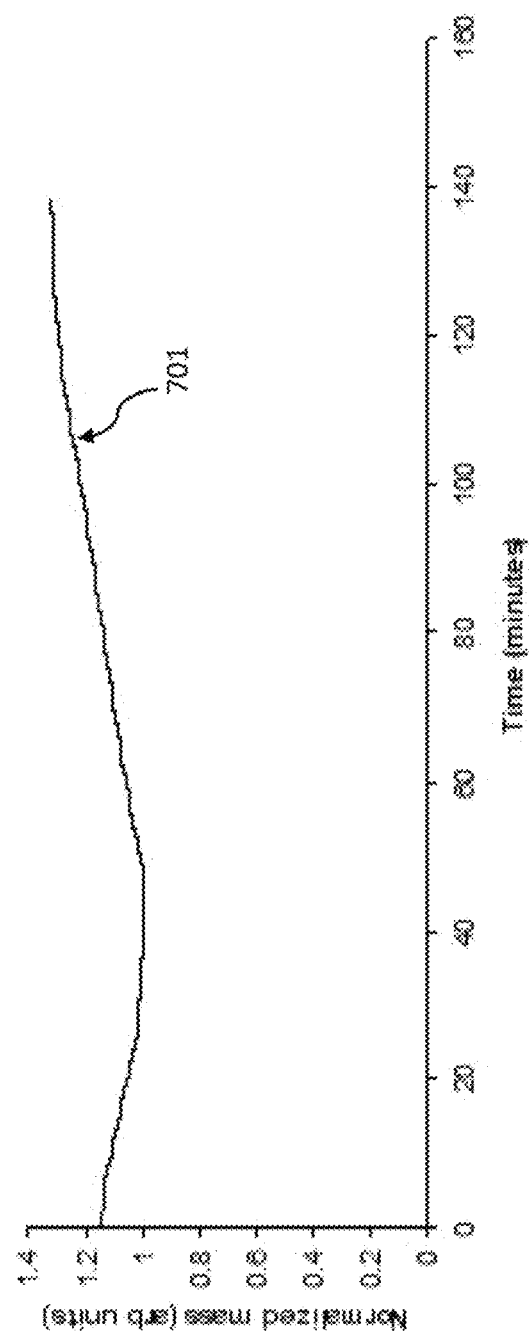
FIG. 7 is a graph that shows the $CO_2$ absorption capacity of PEI-$C_{60}$.

FIG. 7 is a graph that shows the $CO_2$ absorption capacity of the produced PEI-$C_{60}$, and shows the maximum absorption capacity achieved for the produced PEI-$C_{60}$. As can be seen from curve 701, the maximum capacity achieved is ~32% by weight.

Figure 8:
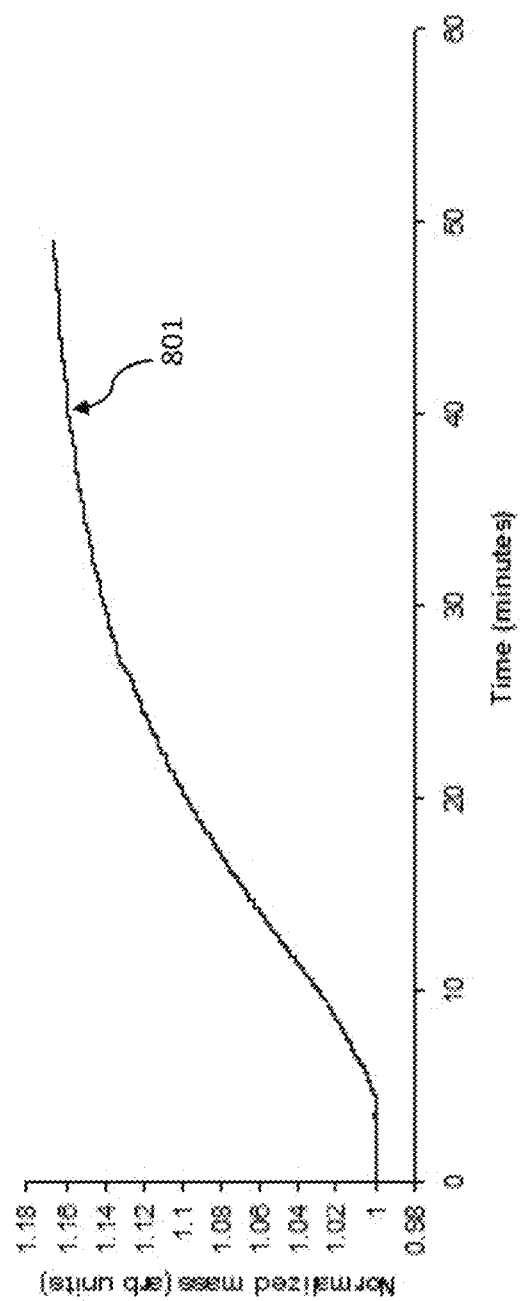
FIG. 8 is a graph that shows the absorption of water of PEI-$C_{60}$.

It is believed that a certain percent of this absorption capacity is attributable to water. To quantify the amount of water captured, the absorption gas was changed from $CO_2$ with a water bubbler to argon with a water bubbler. The result of this absorption capacity test can is shown in the graph of FIG. 8, which graph shows the absorption of water of the produced PEI-$C_{60}$. As we can see from curve 801 of FIG. 8, 16% of the absorbed mass was water.

Figure 9:
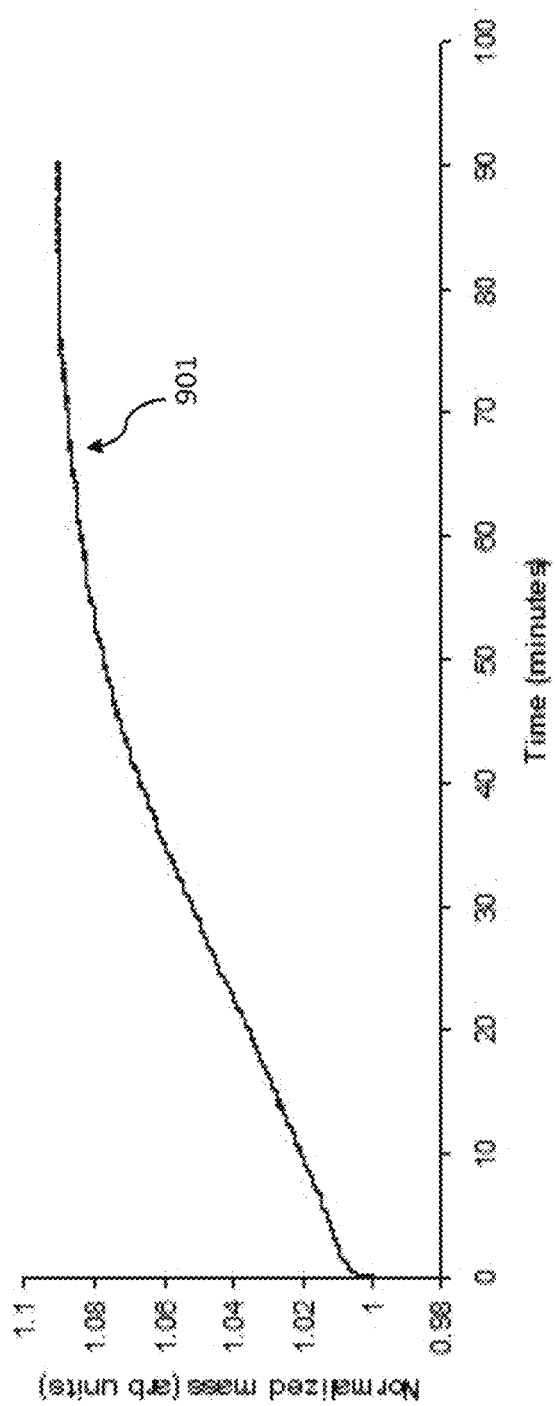
FIG. 9 is a graph that shows the water capacity of PEI-$C_{60}$ using degassed water.

However, the water used was saturated with $CO_2$, and hence this reading was likely high due to the additional absorption of $CO_2$. To determine the actual water capacity of the produced PEI-$C_{60}$, is was necessary to degas the water first. Using the freeze-pump-thaw method the water was degassed and the water absorption experiment was repeated. The results are shown in FIG. 9, which is a graph that shows the water capacity of PEI-$C_{60}$ using degassed water. As curve 901 of FIG. 9 shows, the total amount of degassed water absorbed is ~9%. Knowing that the maximum absorption is ~32% (from the results shown in FIG. 7) and the water is ~9% (from the results shown in FIG. 9), the total $CO_2$ absorbed by the produced PEI-$C_{60}$ was ~23% by weight. Such a absorbance capacity is in excess of any amount previously reported. Applicants are unaware of any material that absorbs nearly one-quarter of its weight in $CO_2$ at ambient pressure and temperature.

Figure 10:
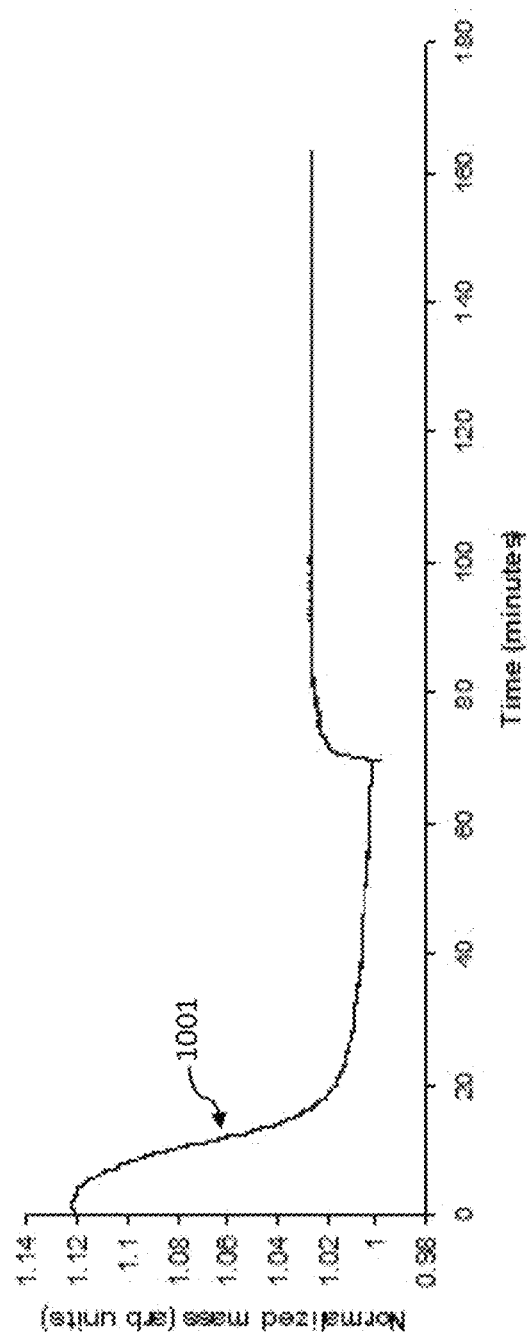
FIG. 10 is a graph that shows the $CO_2$ absorption capacity of a dry PEI-$C_{60}$.

To determine the absorption mechanism (primary, secondary, or tertiary amines), a dry $CO_2$ capture was run, which results are shown in FIG. 10. The reason for this is that water is necessary for the absorption mechanism to occur for tertiary amines (as shown in the mechanism illustrated in FIG. 3), while water is not necessary for the absorption mechanism to occur for primary and secondary amines (as shown in the mechanism illustrated in FIGS. 1-2). FIG. 10 is a graph that shows the $CO_2$ absorption capacity of dry PEI-$C_{60}$. As shown in curve 1001 of FIG. 10, the maximum capacity achieved was ~2%. Knowing that the maximum capacity achieved is 32% when the $CO_2$ is wet and only ~2% when dry, it follows that the primary mode of capture is via tertiary amines. This further confirms that PEI was unfolded and the tertiary amines exposed when producing the PEI-$C_{60}$. Again, the reason for this is that water will only have an effect on the tertiary amines via the mechanism shown in FIG. 3.

Figure 11:
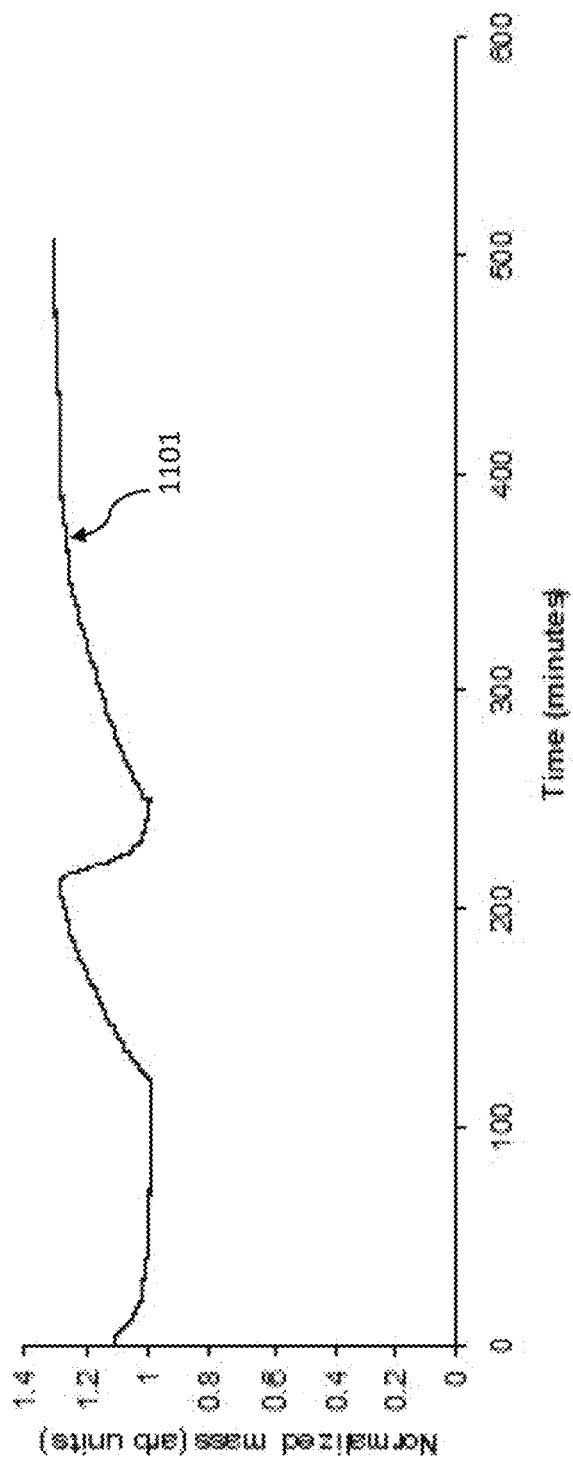
FIG. 11 is a graph that shows the cycle absorption capacity of PEI-$C_{60}$.

A cycling experiment was also run to determine whether the system was regenerable. FIG. 11 is a graph that shows the cycle absorption capacity of PEI-$C_{60}$. As seen in curve 1101 of FIG. 11, the PEI-$C_{60}$ was regenerable.

It has been found that if the reaction with the PEI is not completed such that the PEI is unfolded, the tertiary amines are not properly exposed and the resulting PEI-$C_{60}$ material will not absorb $CO_2$ at ambient temperature and pressure above ~2% by weight (under dry or wet conditions).

Example 2

PEI-$C_{60}$ Material

PEI-$C_{60}$ was alternatively prepared using a method similar to the method described in K. E. Geckler, A. Hirsch, Polymer-bound $C_{60}$, *J. Am. Chem. Soc.*, 1993, 115, 3850.

Example 3

PEI-Graphite Oxide Material

Figure 12:
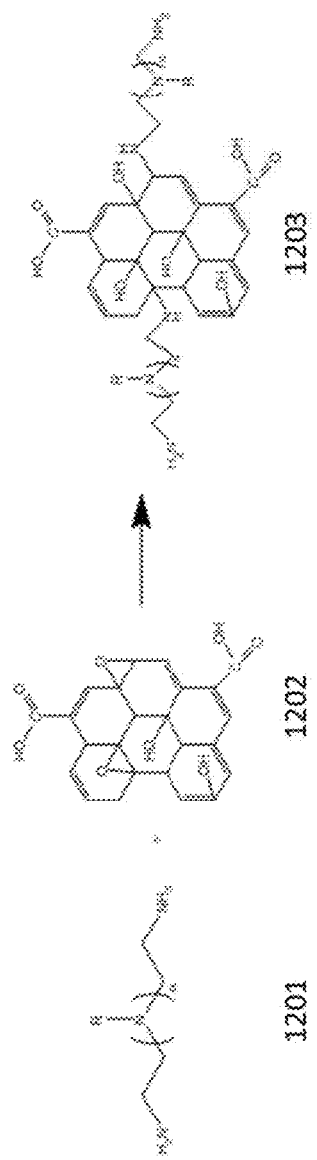
FIG. 12 is a schematic diagram of the reaction of PEI with graphite oxide (GO) to achieve PEI-graphite oxide (PEI-GO).

This schematic diagram for a production method of PEI-GO is shown in FIG. 12. In general, branched polyethyleneimine (25 k Da.) 1201 was dispersed in ethanol via bath sonication. Enough triethylamine (TEA) was added to keep the primary amines of the PEI unprotonated. Concurrently, GO 1202 was dispersed in water. The two solutions were added together and heated to reflux for a period of 7 days with constant stirring. Recovery of the PEI-NC 1203 (PEI-GO) was achieved by filtering the product solution through a 0.2 µm PTFE filter paper and washed with copious amounts of ethanol and water. For $CO_2$ absorption experiments, the recovered PEI-GO was allowed to dry in an oven at 120° C. for a period of 1 hr to remove any water or residual $CO_2$.

Figure 13:
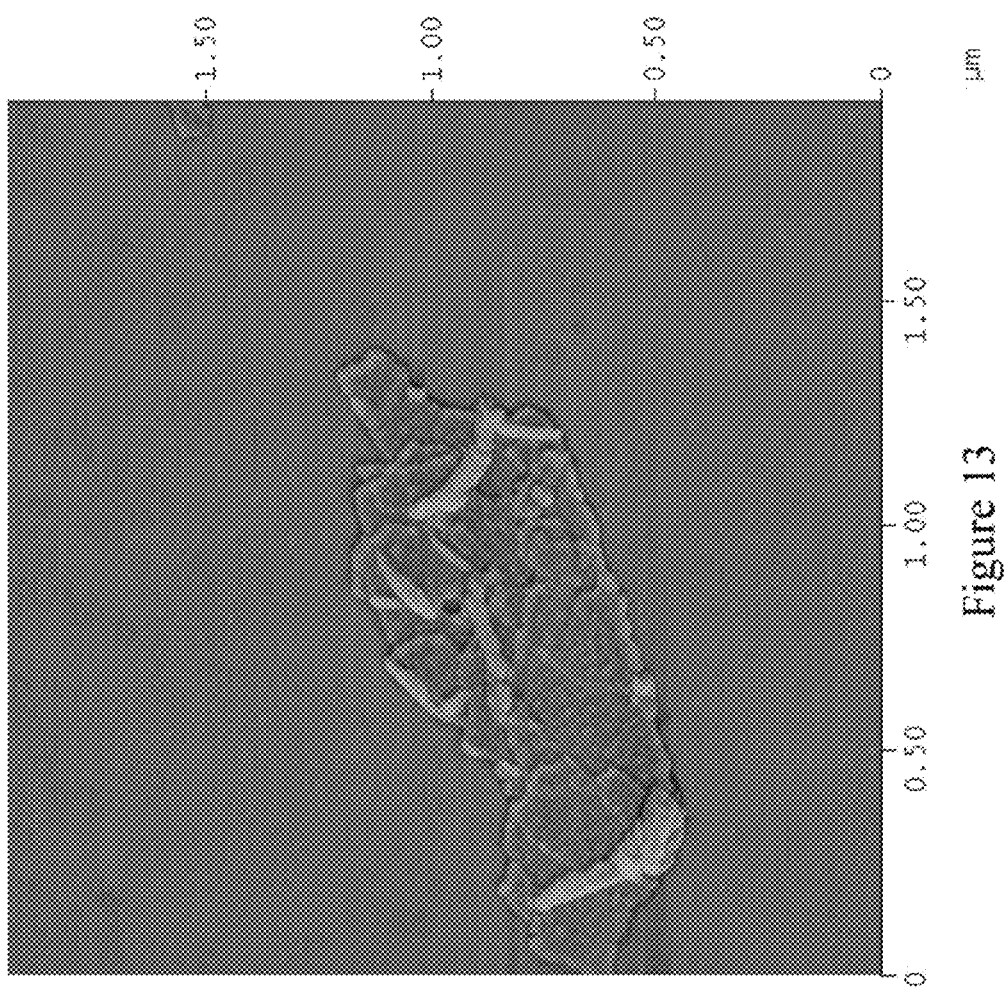
FIG. 13 is an AFM image of PEI-GO.

FIG. 13 is an AFM image of PEI-GO. FIG. 13 shows 0.5-1.5 nm particles comprising of multilayer sheets of a thickness between 30-50 nm.

Figure 14:
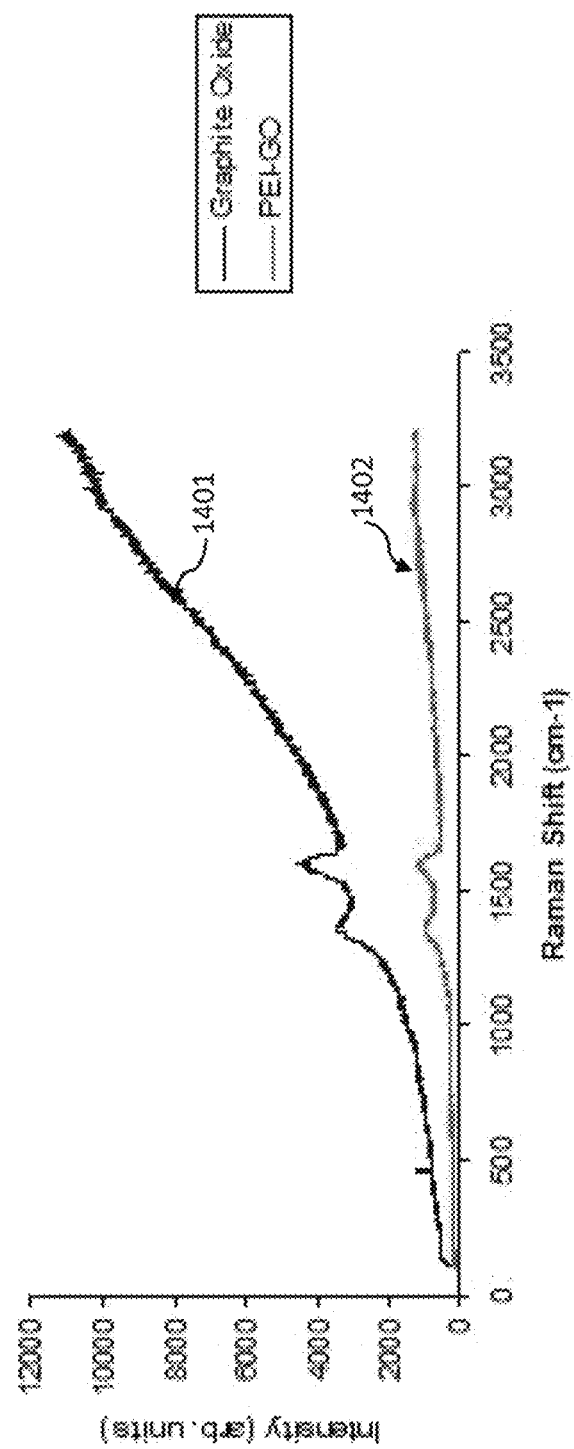
FIG. 14 is a graph that shows the Raman spectra of GO and PEI-GO.
Figure 15A:
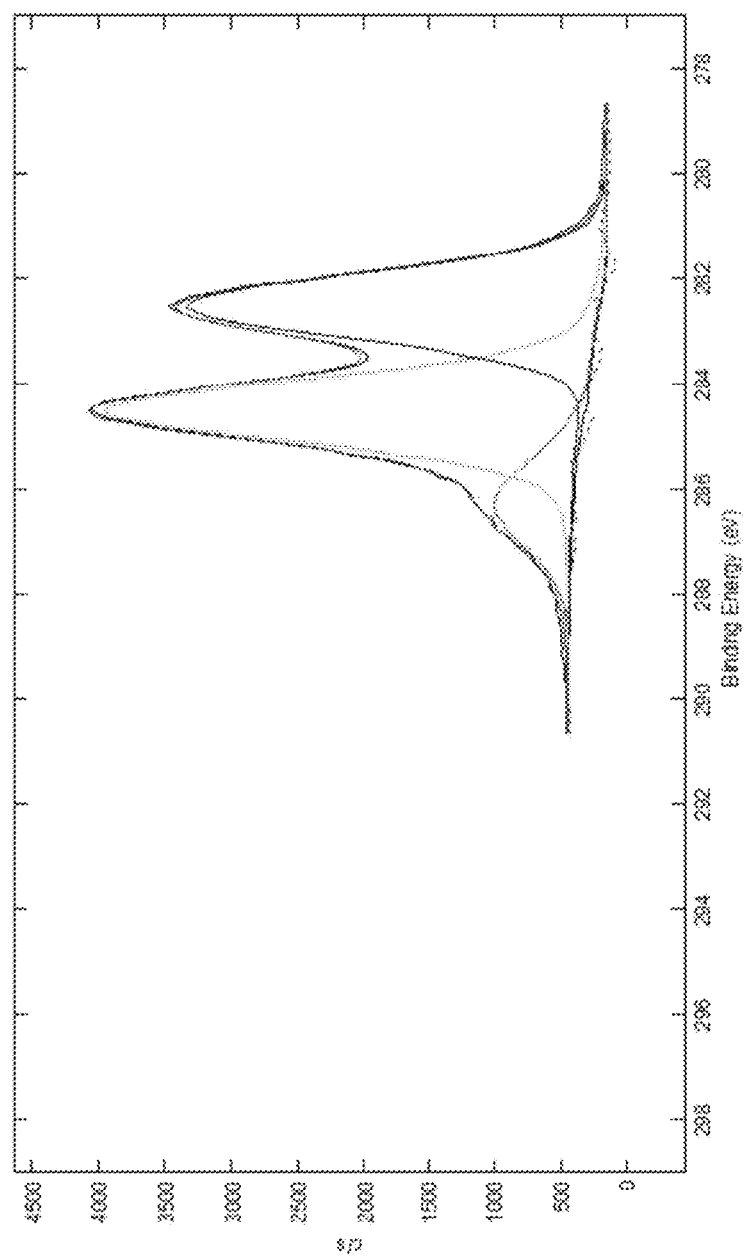
FIG. 15A is a graph that shows the XPS C1s spectra of GO.
Figure 15B:
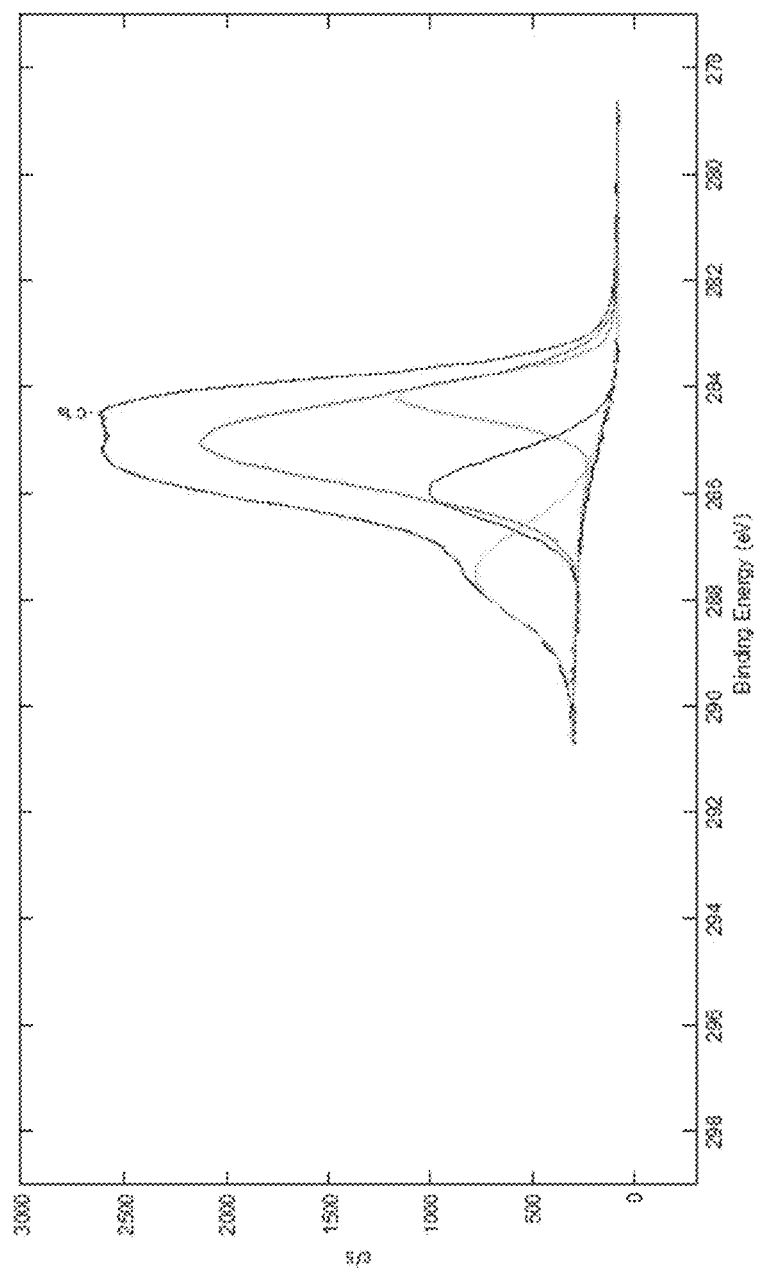
FIG. 15B is a graph that shows the XPS C1s spectra of PEI-GO.
Figure 16A:
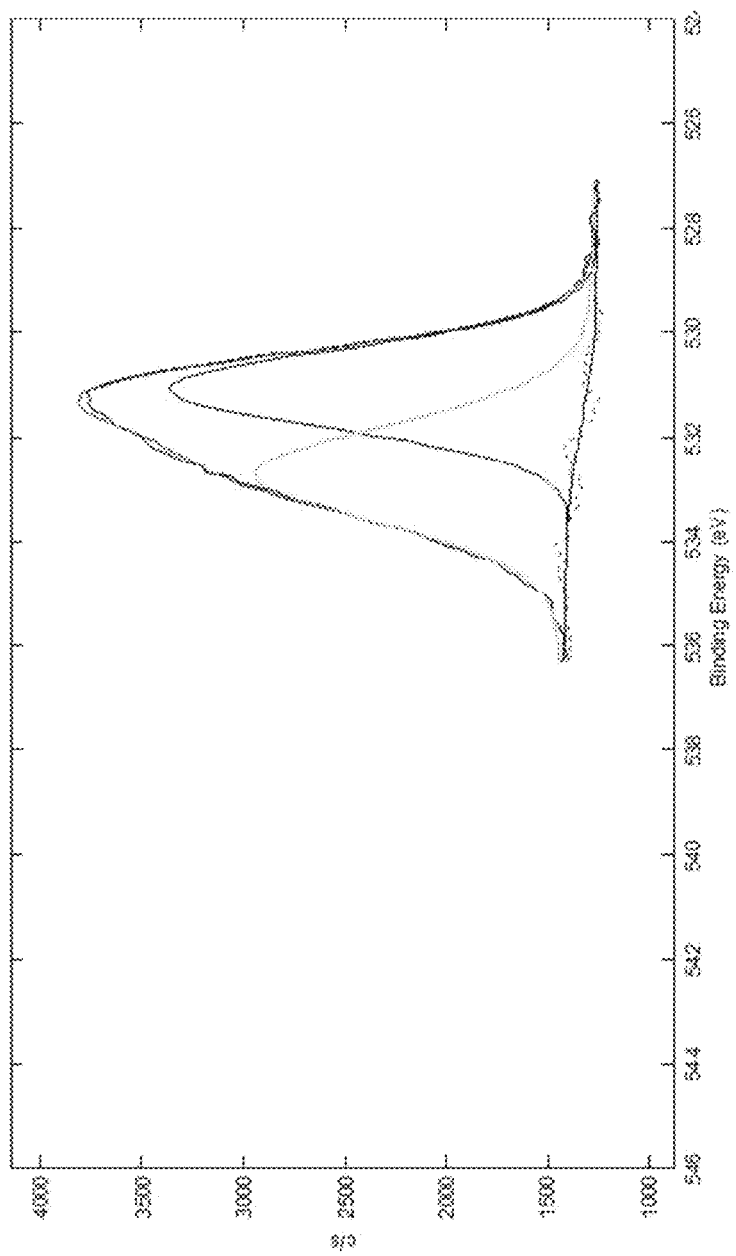
FIG. 16A is a graph that shows the XPS O1s spectra of GO.
Figure 16B:
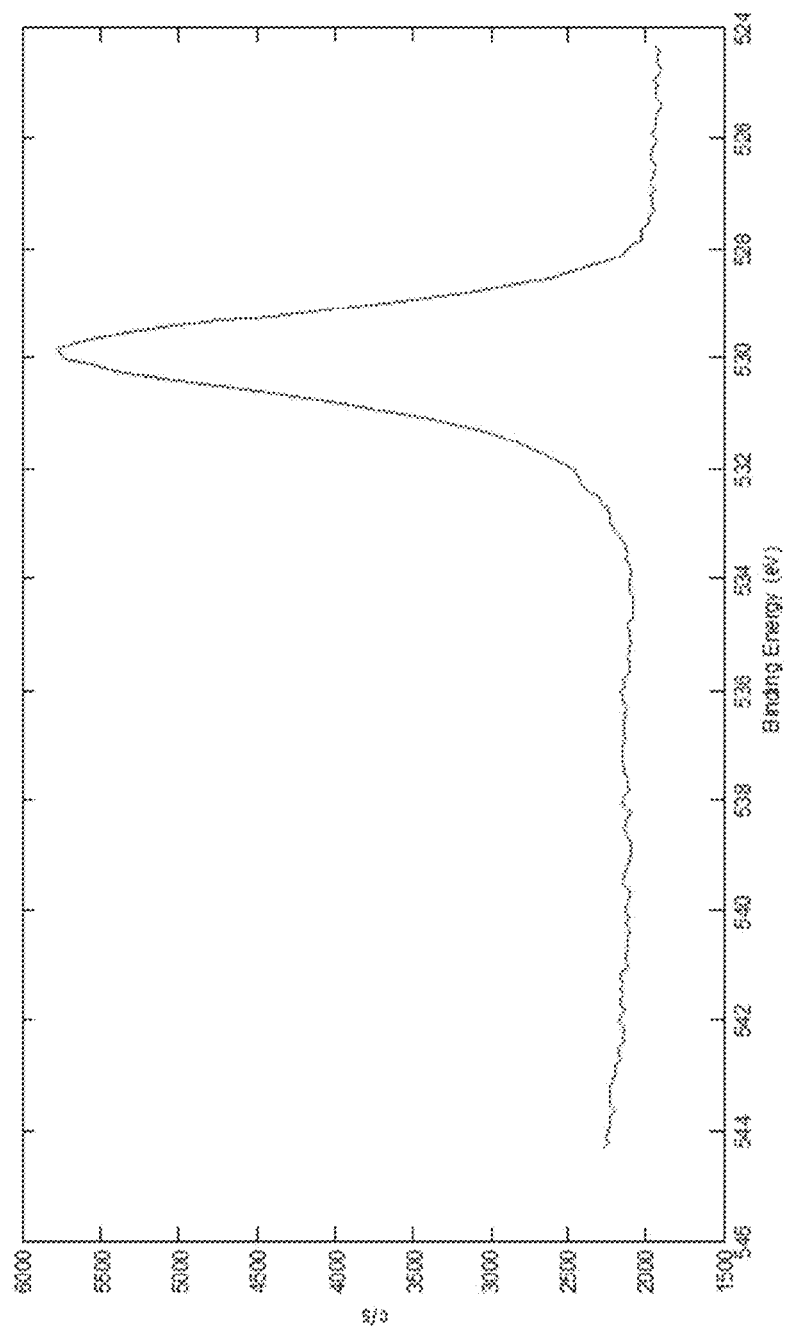
FIG. 16B is a graph that shows the XPS O1s spectra of PEI-GO.

Graphite oxide has previously been functionalized with amino acids via the reaction of amines with the epoxy groups on the basal plane of GO. FIG. 14 is a graph that shows the Raman spectra of GO and PEI-GO (curves 1401 and 1402, respectively). The Raman spectrum of PEI (25000)-GO shows a slight increase in the D:G ratio (0.85) as compared to the GO (0.71), which is consistent with the reaction.

The reappearance of a broad 2D peak (2700 $cm^{-1}$) is consistent with multilayer graphite rather than graphene sheets.

The XPS analysis of PEI (25000)-GO (in FIGS. 15A-15B and 16A-16B) show the presence of significant nitrogen (14.5%) and along, with the TGA (of FIG. 17), indicates a PEI content of approximately 41 wt %. The high resolution C1s spectra show a loss of the C—O peak (287.1 eV) in the GO and the presence of a large shoulder associated with the aliphatic C—N groups in the PEI (286.0 eV).

Figure 17:
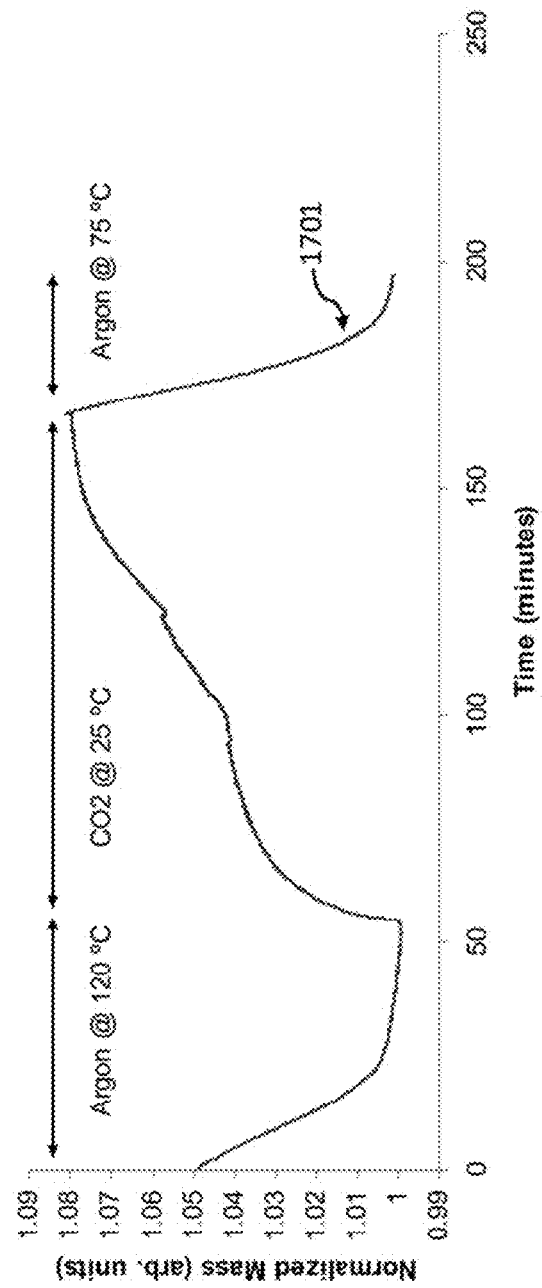
FIG. 17 is a graph that shows the $CO_2$ absorption capacity of PEI-GO.
Figure 18:
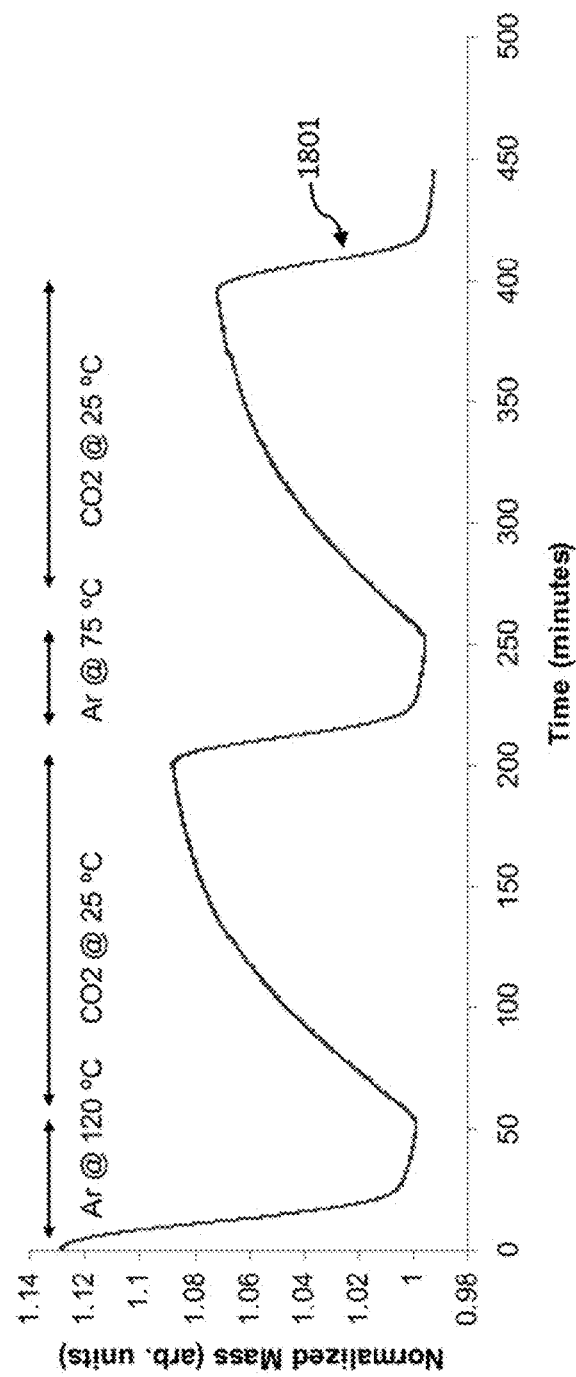
FIG. 18 is a graph that shows the cycle absorption capacity of PEI-GO.

When $CO_2$ comes into contact with the PEI-GO, the $CO_2$ is absorbed onto the PEI-GO leading to an increase in mass of the PEI-GO (~9%), which is shown by the thermogravimetric analysis (TGA) in FIG. 17 (curve 1701). FIG. 18 is a graph that shows the cycle absorption capacity of PEI-GO, and curve 1801 reveals that PEI-GO has the ability to regenerate at low temperatures and be used again.

Example 4

Fluorinated Graphite Intercalation Compounds Functionalized with PEI

The step to synthesize GICs and further modification was performed as follows. Natural graphite powder (99.999% pure) was fluorinated in a custom built fluorination reactor. Initially a vacuum was applied to the fluorination reactor, for a period of thirty minutes to remove any fluorine left in the lines from the last run. After this step, the vacuum was removed and the system was purged with argon. At this point, the reaction chamber was opened and a fluorination pan loaded with the desired amount of graphite (~100-200 mg) was placed in the reaction chamber. The temperature of the system was set to the desired temperature, the temperature of fluorination greatly effects the final composition of the product (T. Nakajima (ed.), Fluorine-carbon and fluoride-carbon materials: Chemistry, physics, and applications. 1995, 1, New York, Marcel Dekker, Inc.). Once the desired temperature was reached the flow gas was changed from argon to 10% fluorine in nitrogen. The flow rate was set to 15 sccm. Additionally a flow of 2% hydrogen in nitrogen was flowed into the reactor at a flow rate of 10 sccm. In this example, fluorination took place at atmospheric pressure. The fluorination was allowed to continue for the desired time also had an effect on the final composition of the product. Once the reaction was complete, the fluorine and hydrogen were turned off and the reactor was then purged with argon at 1000 sccm for a period of about 15 minutes. Vacuum was then pulled on the system for a period of 15 minutes. Argon was then flowed back into the reactor and the reactor is opened and the sample pan was removed and the reactor is sealed.

Graphite intercalation compounds (GIC's) do not have a covalent bonding system between the carbon and fluorine. The bond that was formed was an ionic one; the metallic sidewalls of the reactor and the fluorination pan catalyze the formation of HF ions which then intercalated between the graphitic layers. These ionic carbon fluorine bonds were very labile so characterization and further reactions need to be carried to out quickly to avoid fluorine loss.

PEI can be tethered to the graphite intercalation compounds via the reaction of the lone pair on the amine and the carbons neighboring a carbon with an ionic fluorine bond due to the electronegativity of fluorine. The synthesis steps for this reaction were as follows. Freshly fluorinated GICs (~100 mg) were dispersed in 100 ml of ethanol via bath sonication. Concurrently, PEI (~500 mg) of a chosen molecular weight was also dispersed in ethanol via bath sonication. These two solutions were then combined in a one neck round bottom flask with a Teflon stir bar added. Pyridine (~1 ml) was then added to the reaction to act as a proton shuttle of sorts. The reaction flask was fitted with a condenser and heated to reflux temperature with constant stirring for a period of 5 days. The reaction was recovered by vacuum filtration through a 200 nm pore size PTFE filter paper and washed with copious amounts of ethanol and deionized water before being oven dried at ~120° C.

Figure 19:
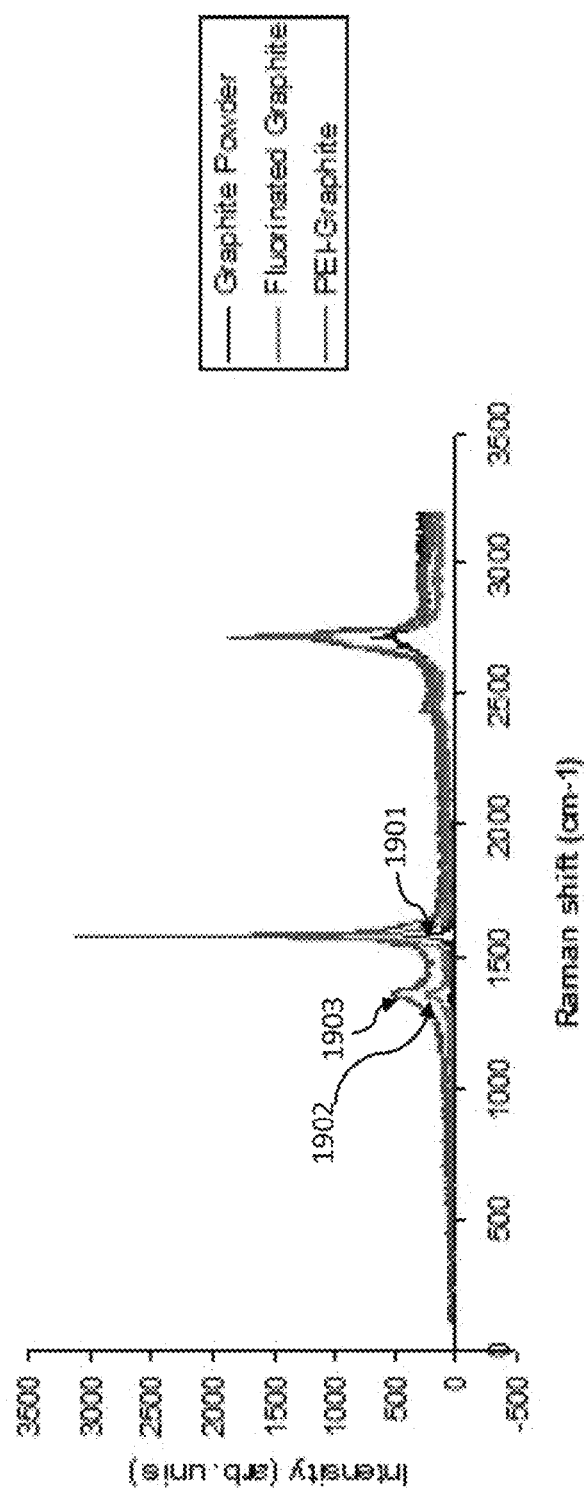
FIG. 19 is a graph that shows the Raman spectra of graphite powder, fluorinated graphite (F-G) and PEI-graphite (PEI-G).

These ionic carbon fluorine bonds are very labile so characterization and further reactions need to be carried out quickly to avoid fluorine loss. Fluorination of natural graphite powder resulted in a material of composition C:F=11-21. FIG. 19 is a graph that shows the Raman spectra of graphite powder, fluorinated graphite (F-G) and PEI-graphite (PEI-G) (curves 1901, 1902, and 1903, respectively). Although the Raman spectrum of the natural graphite has no disorder (D) band, as shown in FIG. 19 both GIC and PEI-GIC do.

The D:G ratio observed upon fluorination (0.11) did not change upon reaction with PEI (0.16). Although the PEI in the PEI-GICs does show uptake of $CO_2$, the amount was very low, as shown in curve 2001 of FIG. 20, which is a graph that shows the $CO_2$ absorption capacity of PEI-F-G.

It is believed that this is in part due to the difficulties in controlling the fluorination reaction and hence the PEI content.

Figure 20:
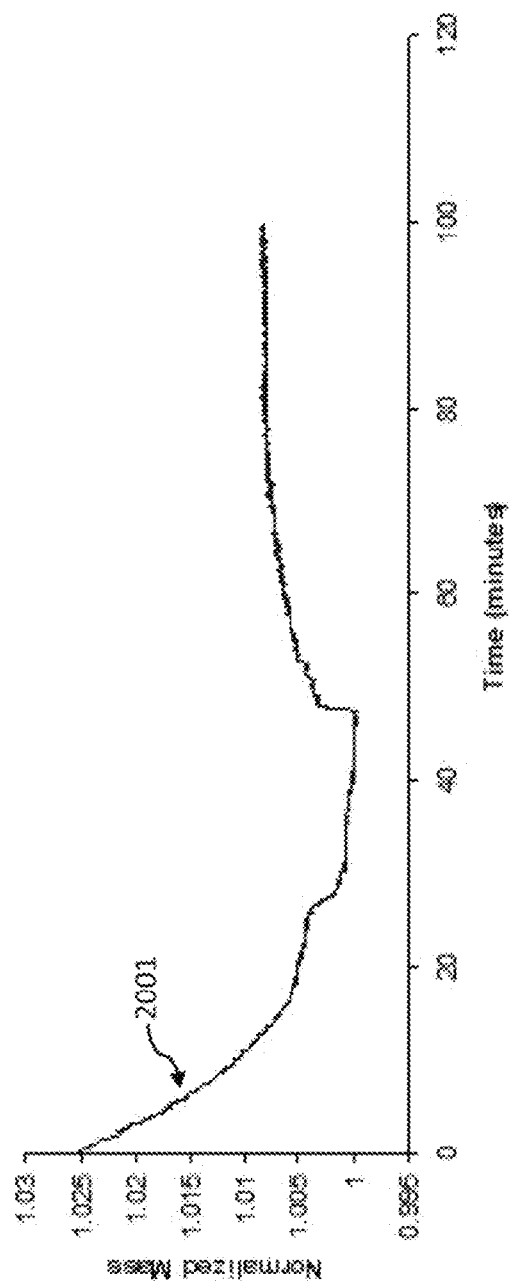
FIG. 20 is a graph that shows the $CO_2$ absorption capacity of PEI-fluorinated graphite (PEI-F-G).

As can be seen by a comparison of FIG. 20 (absorption capacity of PEI-GIC) and FIG. 17 (absorption capacity of PEI-GO), the $CO_2$ absorption rate of PEI-GO is high (~9%) in comparison to the PEI-F-G. However, the rate of absorption is significantly slower for the PEI-GO and the shape of the absorption curve is different to all other absorption runs. This is believed to be caused by the free amines on PEI hydrogen bonding with remaining oxygen containing groups on GO. These oxygen containing groups can be removed by treatment with hydrazine, however, hydrazine treatment will also remove the covalently attached PEI.

Example 5

PEI-Expanded Graphite Material

Expanded graphite was also functionalized with varying molecular weights of PEI by the same method described for the natural graphite GIC.

Example 6

PEI Functionalized Graphite Epoxide

Graphite epoxide was prepared via a previously published literature method. (J. Chattopadhyay, A. Mukherjee, C. E. Hamilton, J. Kang, S. Chakraborty, W. Guo, K. F. Kelly, A. R. Barron, W. E. Billups, Graphite epoxide, *J. Am. Chem. Soc.*, 2008, 130, 5414.) Graphite epoxide (~100 mg) was dispersed in 100 ml of ethanol via bath sonication. Concurrently, PEI of the selected molecular weight (~500 mg) was dispersed in 100 ml of ethanol via bath sonication. Enough triethylamine was added to the PEI solution to ensure 33% of all primary amines in PEI remain unprotonated. These two solutions were then combined in a 250 ml one neck round bottom flask and fitted with a condenser. A stir bar was also added and the reaction was brought to reflux temperature and allowed to stir for a period of 5 days. The recovery of the product was achieved using vacuum filtration of the solution through a 200 nm pore size PTFE filter paper. The product was washed with copious amounts of water and ethanol (~500 ml of each). The product was then oven dried at ~120° C.

Example 7

PEI-Phe-Azide-Graphite Material

Raw graphite can also be used as a starting material. Previous work in the Barron lab (T. A. Strom, E. P. Dillon, C. E. Hamilton, A. R. Barron, Nitrene addition to exfoliated graphene: A one-step route to highly functionalized graphene. *Chem. Commun.*, 2010, 46, 4097.) has shown that raw graphite can be highly functionalized using azide modified phenylanaline. Instead of converting the PEI amines to azides, a previously published method was used to modify the graphite with Boc-Phe(4-$N_3$)—OH. The PEI was then coupled onto the Boc-Phe(4-$N_3$)—OH using a DCC coupling. The $CO_2$ uptake capacity of the PEI-Phe-G is shown in FIG. 21.

Figure 21:
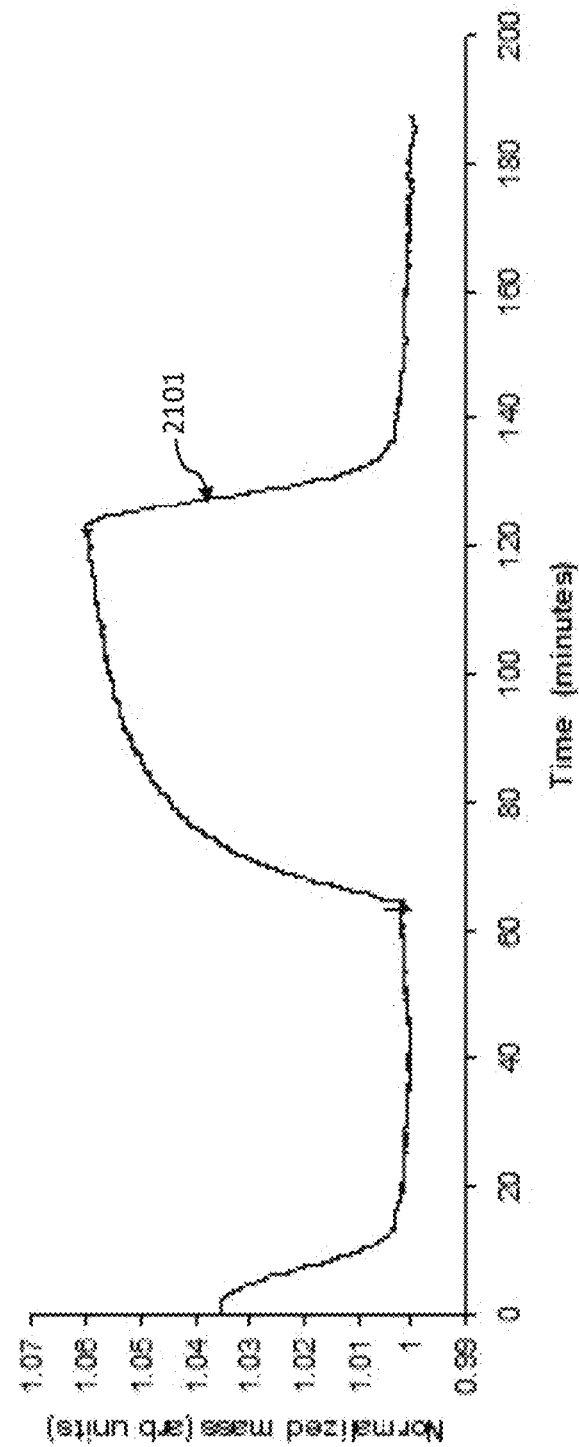
FIG. 21 is a graph that shows the $CO_2$ absorption capacity of PEI-Phe-Azide-Graphite.

As can be seen in curve 2101 of FIG. 21, the absorption capacity is ~6%, however, the rate of absorption is significantly enhanced as compared to PEI-GO.

Example 8

PEI-MWNT Materials

Another base carbon material is multi walled nanotubes, which can be modified in similar ways as SWNTs and are produced in much larger quantities at a significantly cheaper price, as compared to SWNT. PEI-MWNTs were prepared using the same synthesis procedure used for the PEI-SWNTs. The Raman spectra of raw MWNTs and PEI-MWNTs are shown in FIG. 22 (curves 2201 and 2202 for Bay-MWNT and PEI-Bay-MWNT, respectively).

Figure 22:
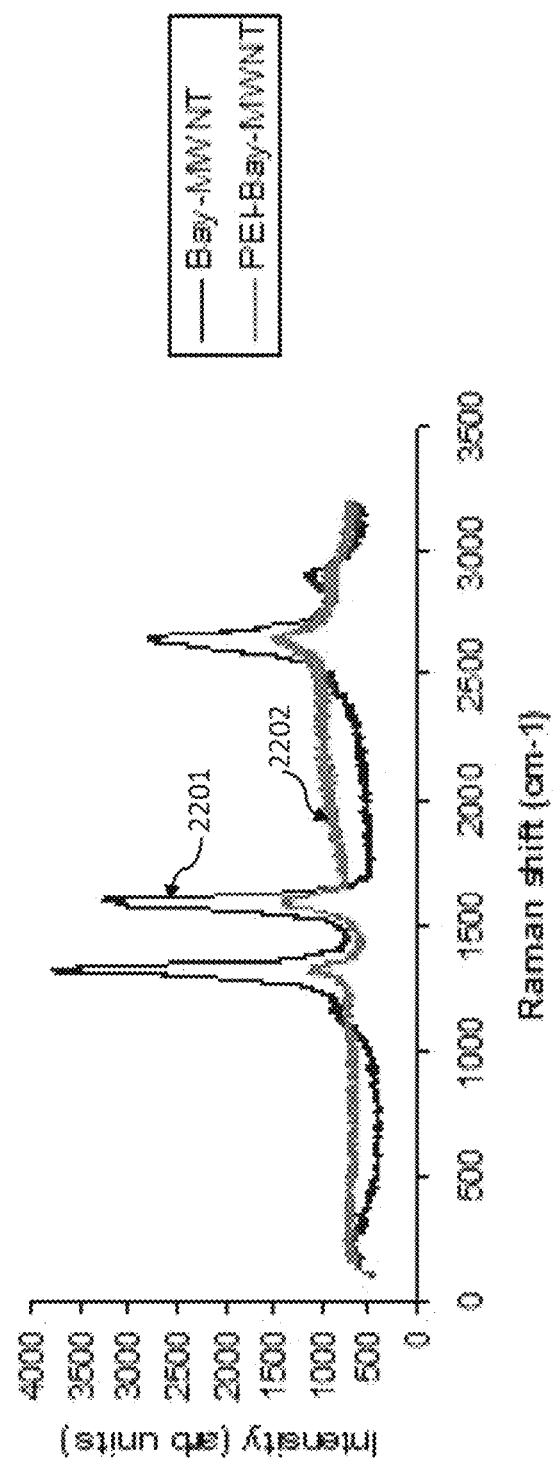
FIG. 22 is a graph that shows the Raman spectra of Bay-MWNT and PEI-Bay-MWNT.

As seen in FIG. 22, the D:G ratio actually decreased after functionalization process, which was the opposite effect as seen when SWNTs are modified. It is believed that the reason for this is that the fluorination process actually "cleans" the MWNTs via the removal by pyrolisys of amorphous carbon that is present in the crude raw MWNT sample. This is similar to the way nanotubes can be cut via fluorination and subsequent pyrolisys.

Figure 23:
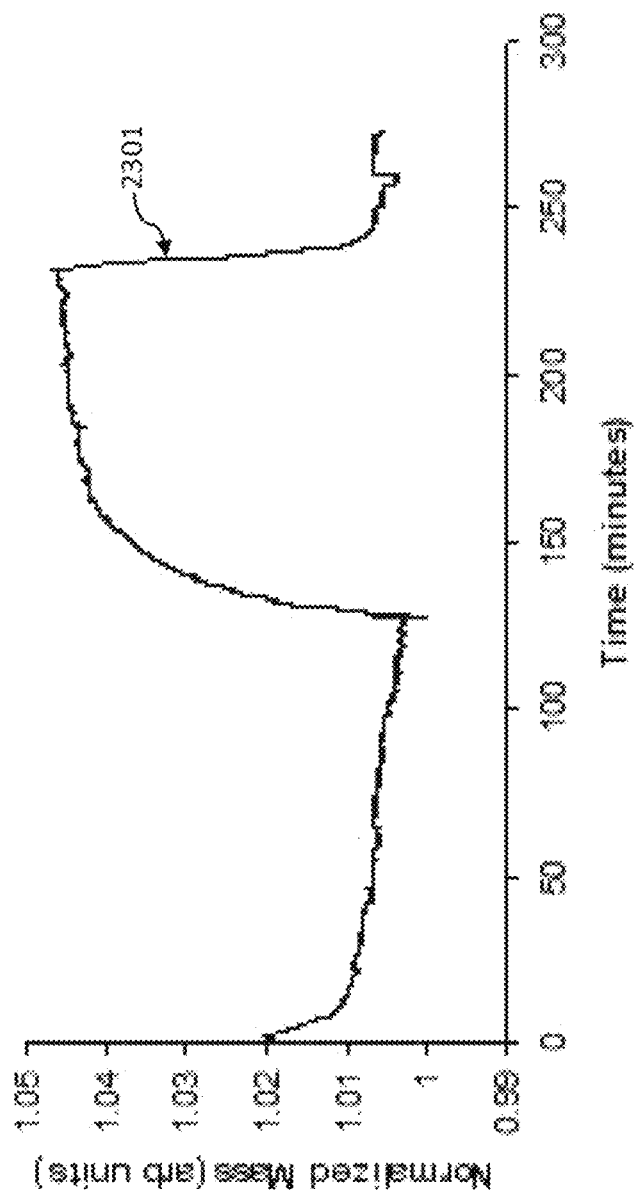
FIG. 23 is a graph that shows the $CO_2$ absorption capacity of PEI-Bay-MWNT.

The $CO_2$ capacity if the PEI functionalized Bay-MWNTs is shown in FIG. 23.

As shown in curve 2301 of FIG. 23, the absorption capacity of PEI-Bay-MWNT is ~5%, which is significantly lower than the capacity achieved with SWNT. The reason for this is that all the interior layers of the MWNT are not functionalized, and hence add weight to the base nanocarbon. This is not the case with SWNTs, as there is only one layer.

Example 9

PEI-Graphite Oxide/PEI-Graphite/PEI-MWNT Comparison

Graphite oxide (GO), graphite (200 mesh) and multiwalled carbon nanotubes (MWNT) were all functionalized with 25,000 Da. branched polyethyleneimine to determine their carbon dioxide absorption potential. X-ray photoelectron spectroscopy (XPS) was used in conjunction with thermogravimetric analysis (TGA) to characterize the degree of functionalization.

TABLE 1

| Sample | % C | % N | % O | % F |
|---|---|---|---|---|
| Fluorinated graphite | 95.6 | 0 | — | 2.4 |
| PEI-fluorinated graphite | 91.7 | 4.5 | — | 0 |
| Graphite oxide | 52.8 | 0 | 47.2 | — |
| PEI-graphite-oxide | 75.1 | 14.5 | 10.4 | — |
| Phe-graphite | 72.8 | 12.8 | 14.3 | — |
| PEI-Phe-graphite | 62.9 | 24.7 | 12.4 | — |

XPS elemental analysis of all samples

As can be seen from Table 1, the highest degree of functionalization was achieved on the graphite oxide and the phenylalanine functionalized 200 mesh graphite. It appears that PEI-Phe-G has the highest nitrogen content (~25%), however, a large part of this figure is already present in the Phe-G substrate (~13%). When these values are compared to the fluorinated graphite it appears that both the GO and Phe-G substrates should absorb higher degrees of $CO_2$ due to the higher degree of PEI functionalization.

Additional PEI-NC Materials.

There are many other ways to prepare a PEI-NC. Further methods exist for the attachment of a polymer to a carbon nanomaterial that can be utilized in embodiments of the present invention. These examples that are provided are not intended to limit the scope of the invention but to illustrate several methods that can be utilized in embodiments of the invention.

For example, as noted above, methods exist to attach amines to graphite oxide (GO) through the reaction of amines with the epoxy group present in GO. (A. B. Bourlinos, D. Gournis, D. Petrdis, T. Szabó, A. Szeri, I. Dékány, Graphite oxide: Chemical reduction to graphite and surface modification with primary aliphatic amines and amino acids. *Langmuir,* 2003, 19, 6050.)

PEI can be adsorbed on to porous graphite (J. H. Knox, Q.-H. Wan, Surface modification of porous graphite for ion exchange chromatography. *Chromatographia,* 1996, 42, 83.)

Amines can be converted into azides for addition onto carbon nanomaterials (P. B. Alper, S. C. Hung, C. H. Wong, Metal catalyzed diazotransfer for the synthesis of azides from amines. *Tetrahedron Lett.,* 1996, 37, 6029.)

A stable diazo transfer reagent could also be synthesized (E. D. Goddard-Borger, R. V. Stick, An efficient, inexpensive, and shelf-stable diazotransfer reagent: Imidazole-1-sulfonyl azide hydrochloride, *Organic Lett.,* 2007, 9, 3797.)

Nitrene addition to carbon nanotubes has already been shown (C. Gao, H. He, L. Zhou, X. Zheng. Y. Zhang, Scalable functional group engineering of carbon nanotubes by improved one-step nitrene chemistry, *Chem. Mater.,* 2009, 21, 360.)

Nitrene addition onto graphite has also been shown (T. A. Strom, E. P. Dillon, C. E. Hamilton, A. R. Barron, Nitrene addition to exfoliated graphene: A one-step route to highly functionalized graphene. *Chem. Commun.,* 2010, 46, 4097.)

Further work using a 1,3-dipolar cycloaddition is another possible route of attachment (A. Padwa, Intramolecular 1,3-dipolar cycloaddition reactions, *Angew. Chem. Int. Edit.,* 1976, 15, 123.)

As noted above, amines themselves can add directly to $C_{60}$ (K. E. Geckler, A. Hirsch, Polymer-bound $C_{60}$, *J. Am. Chem. Soc.,* 1993, 115, 3850.) Also, as noted above, fluorinated nanocarbons will also react with amines tethering the amine to the support structure, for example to a single walled carbon nanotube (E. P. Dillon, C. A. Crouse, A. R. Barron, Synthesis, characterization, and carbon dioxide adsorption of covalently attached polyethyleneimine-functionalized single-wall carbon nanotubes. *ACS Nano,* 2008, 2, 156.)

Graphite can also be fluorinated forming two different classes of graphite-fluorine compounds, graphite fluorides (I. Palchan, M. Crespin, H. Estrade-Szwarckopf, B. Rousseau, Graphite fluoride: An XPS study of a new type of C—F bonding. *Chem. Phys. Lett.,* 1989, 157, 321.) and graphite intercalation compounds (T. Mallouk, N. Barrlett, Reversible Intercalation of graphite fluorine: A New bifluoride, $C_{12}HF_2$ and graphite fluorides, $C_xF$ (5>x>2). *J. Chem. Soc. Chem. Commun.,* 1983, 103.)

Plasma fluorination can also lead to reactions with butylamines (S. B. Bon, L. Valentini, R. Verdejo, J. L. Garcia Fierro, L. Peponi, M. A. Lopez-Manchado, J. M. Kenny, Plasma fluorination of chemically derived graphene sheets and subsequent modification with butylamine *Chem. Mater.,* 2009, 21, 3433.)

Thiol addition has also previously been shown (L. Zhang, J. Zhang, N. Schmandt, J. Cratty, V. N. Khabashesku, K. F. Kelly, A. R. Barron, AFM and STM characterization of thiol and thiophene functionalized SWNT's: pitfalls in the use of chemical markers to determine the extent of sidewall functionalization in SWNT's. *Chem. Commun.* 2005, 5429.)

Sidewall carboxylic acid functionalization on a SWNT has been shown (H. Peng, L. B. Alemany, J. L. Margrave, V. N. Kabashesku, Sidewall carboxylic acid functionalization of single walled carbon nanotubes, *J. Am. Chem. Soc.,* 2003, 125, 15174.)

Additional PEI-NC Materials.

In the example of embodiments of the invention discussed above, PEI was utilized as the amine source. Any other aliphatic amines could also be used in this process instead of PEI.

Absorption of Carbon Dioxide Using PEI-CN

The use of aqueous amine based systems for the absorption of carbon dioxide as been well documents. The separation of $CO_2$ from flue gas is traditionally achieved using aqueous monoethaolamine (MEA) scrubber. This system, however, has several disadvantages, primarily the regeneration of this scrubbing system requires a large amount of energy. In order to regenerate the MEA scrubber, the solution needs to be heated to ~120° C. This temperature manipulation is responsible for up to 80% of the total operating cost of the scrubber system. In order to make a $CO_2$ scrubber system more economically viable, a lower temperature regeneration system is required. This can be achieved using PEI-NC materials, such as a polyethyleneimine-graphite oxide (PEI-GO) membrane system, where regeneration temperatures as low as 70° C. have been achieved. This is illustrated in FIG. 18.

Figure 24:
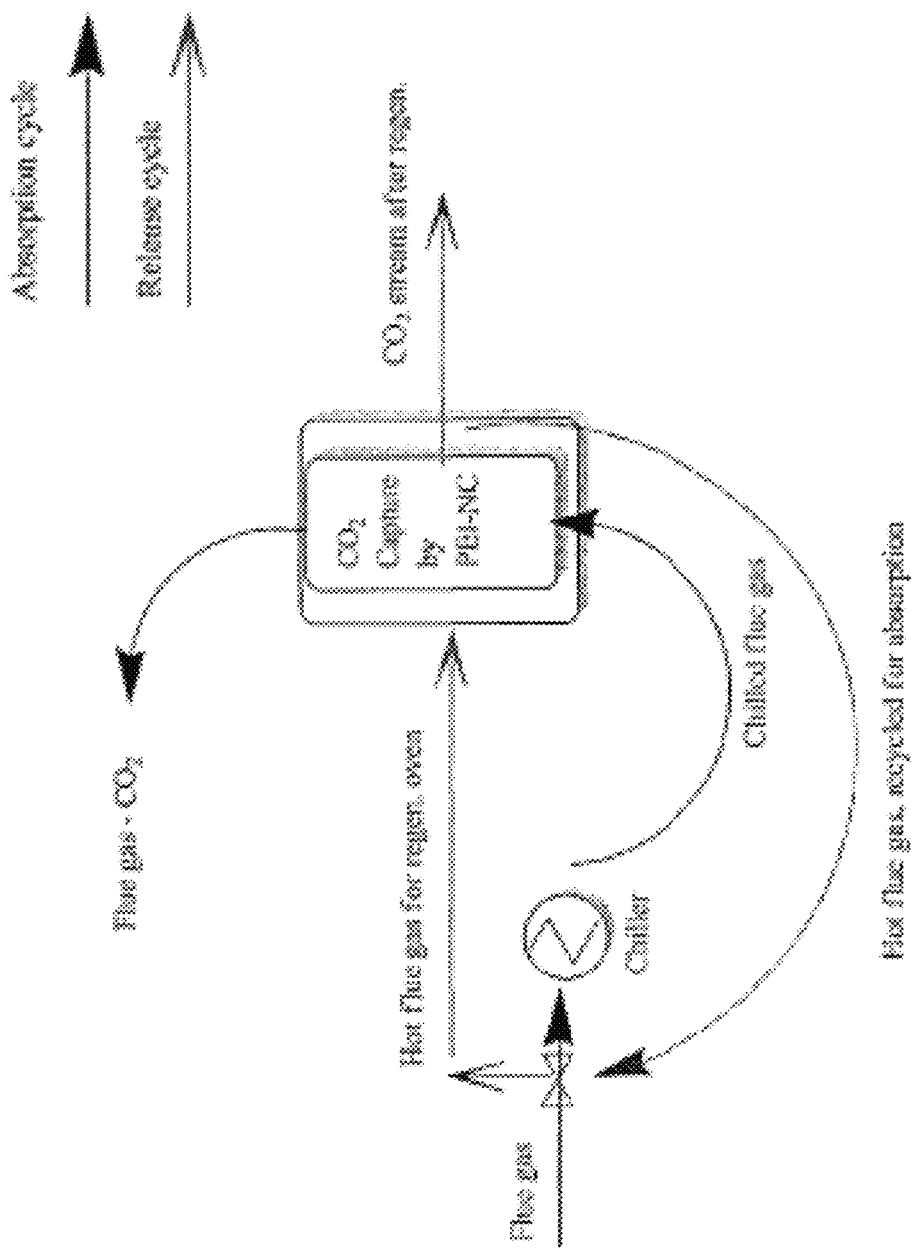
FIG. 24 illustrates the use of an embodiment of the invention in which flue gas is used as the heat source.

Furthermore, this temperature increase can be achieved without having to add additional energy to the system. The flue gas itself could be used as the heat source, which could be diverted from flowing through the scrubber to outside the scrubber which leads to very low operation and maintenance costs. This is illustrated in FIG. 24.

In some embodiments of the invention, a commercially-available pre-purification system that removes certain impurities (like nitrogen oxide and sulfur dioxide) is can be used in series with to the system. This is because impurities like nitrogen oxide and sulfur dioxide can possibly cause irreversible absorptions (which is a problem with all amine based absorbents).

As noted above, there are a number of disadvantages with the current MEA scrubber technology. Among these are that MEA is a corrosive material. This limits the concentration of MEA in water to 30% in order to avoid these corrosive properties. This greatly limits the capacity of the MEA scrubber, which generally achieves a gravimetric capacity of ~7 wt %. Using embodiments of the present invention, a gravimetric capacity of ~9 wt % and ~23 wt % (for PEI-GO and PEI-$C_{60}$, respectively) has been achieved. This alone is more efficient than MEA and has the added benefit of being non-corrosive.

As can be seen from Table 2 below, PEI-NC systems (such as PEI-GO and PEI-$C_{60}$ systems) have several advantages over the current industrial standard for $CO_2$ scrubbing (conventional MEA).

TABLE 2

| | Conventional MEA | PEI-GO | PEI-$C_{60}$ |
|---|---|---|---|
| System Type | Aqueous | Solid Based | Solid Based |
| Absorption Temp. | 50° C. | 20-30° C. | 20-30° C. |
| Regeneration Temp. | 120° C. | 75° C. | 75° C. |
| Gravimetric Capacity | ~7 wt % | ~9 wt % | ~23 wt % |
| Corrosive | Yes | No | No |

For example, the Biofuels Power Corp. green energy power plant in Conroe, Tex., produces a flue gas stream with a flow rate of 695,000 lbs/hr. Of this flue gas stream, the flow rate of $CO_2$ is 7.35 tons/hr or 52,920 tons/year. (These numbers do not account for the additional turbine installations; rather this example is for a single turbine plant).

This means a $CO_2$ scrubber system will need to absorb 180 tons of $CO_2$ per day. With a 10 wt % gravimetric capacity, the system will need to be 1800 tons. It is believe that the capital costs of the system of an embodiment of the present invention, (which include the graphite oxide material and polyethyleneimine (PEI)), would currently total ~$12.4 million. The operating cost associated with such a system would be considerably less that those associated with a monoethanolamine (MEA) system. MEA systems require a large energy penalty to regenerate the system ($15 per ton $CO_2$ absorbed).

An embodiment of the present invention will not require such costs, as the system can be regenerated at a much lower temperature, 75° C. compared to 120° C. for MEA. Furthermore the MEA is a liquid based system. This means that the $CO_2$ must be separated from the steam flow after it has been regenerated, and the solvent needs to be constantly replaced. None of these costs associated with MEA will be required in the embodiment of the present invention (such as a PEI-GO system).

The total cost for the PEI-GO carbon system with capital, operation and maintenance costs is ~$44 per ton of $CO_2$ absorbed. When this is compared to the current MEA system with an operating and maintenance cost of $70 per ton $CO_2$ and a capital cost of at least $50 per ton $CO_2$ absorbed giving a minimum total of $120 per ton of $CO_2$, it can be seen that the PEI-GO system will be significantly more economic.

As for other process currently being used, there are likewise disadvantages when compared to embodiments of the present invention.

Absorption Processes.

Adsorption processes using material such as $HSC^+$, which is currently used to scrub $CO_2$ from the space shuttle, also have several disadvantages. Firstly, these systems can only handle low concentrations of $CO_2$ (<1.5%). Furthermore, the adsorbent materials are not selective to $CO_2$, as it is a pore based system any molecule smaller than $CO_2$ can also fill up the space in the pores that is for adsorption. (See Aaron)

Cryogenic Distillation.

As is expected, the cryogenic distillation process is a very energy intensive one, which leads to very high operating costs. Also, the stream for cryogenic distillation must be free of all contaminants as any $H_2O$ present in the system could possibly freeze and plug all the pipes. Water in this system may also corrode the system. (See Aaron)

Membrane Diffusion.

Membrane based scrubbers are similar to those based on the adsorption process, neither are selective towards $CO_2$. Membranes can be made that are very selective to $CO_2$, however, when this is achieved the membranes then become impermeable to $CO_2$. Furthermore the use of organic membranes means that the scrubber will not perform well at high temperatures such as those associated with the flue gas stream itself (See Aaron).

Hydrate Formation.

The very reason research into using hydrates for $CO_2$ capture started is also a large drawback. When transporting natural gas through areas of low temperature and under pressure hydrates were formed and they plugged the pipes. Furthermore in bench scale tests to capture $CO_2$ hydrates formed and plugged the testing apparatus. Additionally the efficiency of this system is very low, only 35% of the $CO_2$ that entered the reactor was actually captured. (See Aaron)

General TGA Procedure.

Characterization of the $CO_2$ absorption potential of the PEI-NCs was pre-formed on a Seiko TG/DTA 200. The general procedure for all PEI-NCs was performed as follows. Two platinum TGA pans are placed on the balance arms of the TGA, the chamber was sealed and purged with a steady flow of argon and then the mass is then zeroed. The sample pan was then removed while the reference pan was left untouched. The sample pan was then loaded with between 5 and 10 mg of the PEI-NC being tested. The sample pan was then placed back on the balance arm. The mass was allowed to reach a steady state and then the initial mass of the PEI-NC is recorded. The temperature program was then set for an initial temperature ramp from 25° C. to 120° C. at a rate of 5° C. $min^{-1}$ with a hold time at 120° C. of 1 hour. This step burned off any residual moisture or $CO_2$ present in the system. After the initial hold, the temperature program decreased the temperature to 25° C. at a rate of 5° C. $min^1$ with a hold time at 25° C. of 2 hours for $CO_2$ absorption. When the temperature reached 25° C., the feed gas was changed from argon to $CO_2$. A mass increase was evident on the TGA curve as the $CO_2$ was absorbed by the PEI-NC. Once the maximum absorption capacity was reached, indicated by a stabilized mass, the gas was changed back to argon and the temperature program increased the temperature of the system to 75° C. at a rate of 5° C. $min^{-1}$ in order to demonstrate scrubber regeneration. To demonstrate the cycling ability of the PEI-NC scrubber, the temperature was then decreased back to 25° C., and the gas was once again changed from argon to $CO_2$ and absorption occurs. The regeneration step was then repeated to regenerate the scrubber once again.

While various preferred embodiments of the invention have been shown and described, modifications thereof can be made by one skilled in the art without departing from the scope of the invention. The examples described herein are merely illustrative, and are not limiting. For example, various amine terminated polymers, different molecular weight PEI and various nanocarbons can be used. Likewise, the solvents, washes and temperatures of the processing step can be varied, so long as the desired composition is formed. Accordingly the scope of protection is not limited by the description set out above, but is only limited by the claims that follow and include all equivalents of the subject matter of the claims. In any method claim, the recitation of steps in a particular order is not intended to limit the scope of the claim to the performance of the steps in that order, or to require completion of one step prior to the commencement of another step, unless so stated in the claim.

The disclosures of all patents, patent applications, and publications cited herein are hereby incorporated herein by reference in their entirety, to the extent that they provide exemplary, procedural, or other details supplementary to those set forth herein.

What is claimed is:

1. A composition comprising:
   a nanocarbon support, wherein the nanocarbon support is selected from the group consisting of graphite intercalation compounds, graphite oxide, and combinations thereof; and
   a polyethyleneimine attached to the nanocarbon support to form a polyethyleneimine-nanocarbon material.

2. The composition of claim 1, wherein the polyethyleneimine-nanocarbon material has a $CO_2$ absorption capacity at ambient pressure and temperature of at least about 10 wt % of the polyethyleneimine-nanocarbon material.

3. The composition of claim 1, wherein the polyethyleneimine-nanocarbon material has a $CO_2$ absorption capacity at ambient pressure and temperature of at least about 10 wt % of the polyethyleneimine-nanocarbon material.

4. The composition of claim 1, wherein the polyethyleneimine-nanocarbon material has a $CO_2$ absorption capacity at ambient pressure and temperature of at least about 15 wt % of the polyethyleneimine-nanocarbon material.

5. The composition of claim 1, wherein the polyethyleneimine-nanocarbon material has a $CO_2$ absorption capacity at ambient pressure and temperature of at least about 20 wt % of the polyethyleneimine-nanocarbon material.

6. The composition of claim 1, wherein the polyethyleneimine-nanocarbon material has a $CO_2$ absorption capacity at ambient pressure and temperature between about 20 wt % and about 25 wt % of the polyethyleneimine-nanocarbon material.

7. The composition of claim 1, wherein
   the nanocarbon support comprises graphite oxide; and
   the polyethyleneimine-nanocarbon material comprises a polyethyleneimine-graphite oxide material.

8. The composition of claim 1, wherein
   the nanocarbon support comprises a graphite intercalation compound; and
   the polyethyleneimine-nanocarbon material comprises a polyethyleneimine-graphite intercalation compound material.

9. The composition of claim 1, wherein the polyethyleneimine in the polyethyleneimine-nanocarbon material is unfolded.

10. The composition of claim 1, wherein the ratio of (a) tertiary amines of the polyethyleneimine-nanocarbon material operable for absorbing $CO_2$ at ambient pressure and temperature to (b) primary amines and secondary amines of the polyethyleneimine-nanocarbon material operable for absorbing $CO_2$ at ambient pressure and temperature is at least about 5:1.

11. The composition of claim 10, wherein the ratio is at least about 10:1.

* * * * *